(12) United States Patent
Otto et al.

(10) Patent No.: US 8,073,103 B2
(45) Date of Patent: Dec. 6, 2011

(54) SYSTEMS AND METHODS FOR OPTIMIZATION OF ON-LINE ADAPTIVE RADIATION THERAPY

(75) Inventors: Karl Otto, Vancouver (CA); Ante Mestrovic, Vancouver (CA)

(73) Assignee: British Columbia Cancer Agency Branch, Vancouver (CA)

( * ) Notice: Subject to any disclaimer, the term of this patent is extended or adjusted under 35 U.S.C. 154(b) by 174 days.

(21) Appl. No.: 12/374,788

(22) PCT Filed: Jul. 27, 2007

(86) PCT No.: PCT/CA2007/001339
§ 371 (c)(1),
(2), (4) Date: Jan. 22, 2009

(87) PCT Pub. No.: WO2008/011725
PCT Pub. Date: Jan. 31, 2008

(65) Prior Publication Data
US 2010/0020931 A1   Jan. 28, 2010

Related U.S. Application Data

(60) Provisional application No. 60/820,582, filed on Jul. 27, 2006.

(51) Int. Cl.
*A61N 5/10* (2006.01)
(52) U.S. Cl. ......................................................... 378/65
(58) Field of Classification Search ...................... 378/65
See application file for complete search history.

(56) References Cited

U.S. PATENT DOCUMENTS 3,987,281 A   10/1976 Hodes
4,868,843 A   9/1989 Nunan
4,868,844 A   9/1989 Nunan
5,027,818 A   7/1991 Bova et al.
5,332,908 A   7/1994 Weidlich
5,591,983 A   1/1997 Yao
5,647,663 A   7/1997 Holmes (Continued)

FOREIGN PATENT DOCUMENTS

WO   9948558   9/1999

(Continued)

OTHER PUBLICATIONS

Yan, D. et al., "Computed tomography guided management of interfractional patient variation", Semin. Radiat, Oncol. 15, 168-179 (2005).

(Continued)

*Primary Examiner* — Glen Kao
(74) *Attorney, Agent, or Firm* — Oyen Wiggs Green & Mutala LLP

(57) ABSTRACT

Methods and systems are disclosed for radiation treatment of a subject involving one or more fractional treatments. A fractional treatment comprises: obtaining fractional image data pertaining to a region of interest of the subject; performing a fractional optimization of a radiation treatment plan to determine optimized values of one or more radiation delivery variables based at least in part on the fractional image data; and delivering a fraction of the radiation treatment plan to the region of interest using the optimized values of the one or more radiation delivery variables as one or more corresponding parameters of the radiation treatment plan. A portion of performing the fractional optimization overlaps temporally with a portion of at least one of: obtaining the fractional image data and delivering the fraction of the radiation treatment plan.

61 Claims, 5 Drawing Sheets

U.S. PATENT DOCUMENTS

| | | | |
|---|---|---|---|
| 5,663,999 | A | 9/1997 | Siochi |
| 5,748,703 | A | 5/1998 | Cosman |
| 5,757,881 | A | 5/1998 | Hughes |
| 5,802,136 | A | 9/1998 | Carol |
| 5,818,902 | A | 10/1998 | Yu |
| 6,038,283 | A | 3/2000 | Carol et al. |
| 6,052,430 | A | 4/2000 | Siochi et al. |
| 6,108,400 | A | 8/2000 | Siochi |
| 6,134,296 | A | 10/2000 | Siochi |
| 6,142,925 | A | 11/2000 | Siochi et al. |
| 6,240,161 | B1 | 5/2001 | Siochi |
| 6,260,005 | B1 | 7/2001 | Yang et al. |
| 6,278,766 | B1 | 8/2001 | Kooy et al. |
| 6,314,159 | B1 | 11/2001 | Siochi |
| 6,330,300 | B1 | 12/2001 | Siochi |
| 6,335,961 | B1 | 1/2002 | Wofford et al. |
| 6,349,129 | B1 | 2/2002 | Siochi |
| 6,385,477 | B1 | 5/2002 | Werner et al. |
| 6,393,096 | B1 | 5/2002 | Carol et al. |
| 6,411,675 | B1 * | 6/2002 | Llacer ............................. 378/65 |
| 6,473,490 | B1 | 10/2002 | Siochi |
| 6,504,899 | B2 | 1/2003 | Pugachev et al. |
| 6,560,311 | B1 | 5/2003 | Shepard et al. |
| 6,661,870 | B2 | 12/2003 | Kapatoes et al. |
| 6,757,355 | B1 | 6/2004 | Siochi |
| 6,792,074 | B2 | 9/2004 | Erbel et al. |
| 6,907,105 | B2 | 6/2005 | Otto |
| 7,085,348 | B2 | 8/2006 | Kamath et al. |
| 7,162,008 | B2 | 1/2007 | Earl et al. |
| 7,333,591 | B2 | 2/2008 | Earl et al. |
| 2002/0006182 | A1 | 1/2002 | Kim et al. |
| 2002/0150207 | A1 * | 10/2002 | Kapatoes et al. ................ 378/65 |
| 2003/0086528 | A1 * | 5/2003 | Bova ............................... 378/65 |
| 2003/0086530 | A1 | 5/2003 | Otto |
| 2004/0001569 | A1 * | 1/2004 | Luo ................................. 378/65 |
| 2004/0071261 | A1 | 4/2004 | Earl et al. |
| 2004/0254448 | A1 | 12/2004 | Amies et al. |
| 2005/0096515 | A1 | 5/2005 | Geng |
| 2006/0067469 | A1 * | 3/2006 | Dooley et al. ................... 378/65 |
| 2006/0256915 | A1 | 11/2006 | Otto et al. |
| 2008/0298550 | A1 | 12/2008 | Otto |
| 2009/0161827 | A1 | 6/2009 | Gertner et al. |
| 2010/0020931 | A1 | 1/2010 | Otto et al. |

FOREIGN PATENT DOCUMENTS

| | | |
|---|---|---|
| WO | 0015299 | 3/2000 |
| WO | 0160236 | 8/2001 |
| WO | 0224277 | 3/2002 |

OTHER PUBLICATIONS

Court, L. et al., "An automatic CT-guided adaptive radiation therapy technique by on-line modification of MLC leaf positions for prostate cancer", Int. J. Radiat. Oncol., Biol., Phys. 62(1), 154-163 (2005).

Mohan, R. et al., "Use of deformed intensity distributions for on-line modification of image-guided IMRT to account for interfractional anatomic changes", Int. J. Radiat. Oncol., Biol., Phys. 61(4), 1258-1266 (2005).

Mackie, T.R. et al., "Image guidance for precise conformal radiotherapy", Int. J. Radiat. Oncol., Biol., Phys. 56(1), 89-105 (2003).

Brock, K.K. et al., "Feasibility of a novel deformable image registration technique to facilitate classification, targeting, and monitoring of tumor and normal tissue", Int. J. Radiat. Oncol., Biol., Phys. 64(4), 1245-1254 (2006).

Davis, B.C. et al., "Automatic segmentation of intra-treatment CT images for adaptive radiation therapy of the prostate", Med. Image Comput. Comput. Assist. Interv. Int. Conf. Med. Image. Comput. Comput. Assist Interv. 8(Pt 1), 442-450 (2005).

Foskey, M., "Large deformation three-dimensional image registration in image-guided radiation therapy", Phys. Med. Biol. 50(24), 5869-5892 (Dec. 7, 2005).

Munbodh, R. et al., "Automated 2D-3D registration of a radiograph and a cone beam CT using line-segment enhancement", Med. Phys. 33(5), 1398-1411 (Apr. 27, 2006).

Court, L.E. et al., "Automatic online adaptive radiation therapy techniques for targets with significant shape change: A feasibility study", Phys. Med. Biol. 51(10), 2493-2501 (Apr. 27, 2006).

De Gersem, W. et al., "Leaf position optimization for step-and-shoot IMRT", Int. J. Radiat. Oncol., Biol., Phys. 51(5), 1371-1388 (2001).

Shepard, D.M. et al., "Direct aperture optimization: A turnkey solution for step-and-shoot IMRT", Med. Phys. 29(6), 1007-1018 (2002).

Cotrutz, C. et al., "Segment-based dose optimization using a genetic algorithm", Phys. Med. Biol. 48(18), 2987-2998 (2003).

Bedford, J.L. et al., "Constrained segment shapes in direct-aperture optimization for step-and shoot IMRT", Med. Phys. 33(4). 944-958 (Mar. 17, 2006).

Kirkpatrick, S. et al., "Optimization by simulated annealing", Science 220, 671-680 (1983).

I.M.R.T.C.W. Group, "Intensity-modulated radiotherapy: Current status and issues of interest", Int. J. Radiat. Oncol., Biol., Phys. 51(4), 880-914 (2001).

Niemierko, A. et al, "Random sampling for evaluation treatment plans", Med. Phys. 17(5), 753-762 (1990).

Chui, C.S. et al., "Dose calculation for photon beams with intensity modulation generated by dynamic jaw or multileaf collimations", Med. Phys, 21(8), 1237-1244 (1994).

Ghilezan, M.J. et al., "Prostate gland motion assessed with cine-magnetic resonance imaging (cine-MRI)", Int. J. Radiat. Oncol., Biol., Phys. 62(2), 406-417 (2005).

Nichol, A.M. et al., "Intra-prostatic fiducial markers and concurrent androgen deprivation", Clin. Oncol. (R Coll. Radiol) 17(6), 465-468 (2005).

Zellars, R.C. et al., "Prostate position late in the course of external beam therapy: Patterns and predictors", Int. J. Radiat. Oncol., Biol., Phys. 47(3), 655-660 (2000).

Sanguineti, G. et al., "Neoadjuvant androgen deprivation and prostate gland shrinkage during conformal radiotherapy", Radiother, Oncol. 66(2), 151-157 (2003).

Nichol, A.M. et al., "A magnetic resonance imaging study of prostate deformation relative to implanted gold fiducial markers", Int. J. Radiat. Oncol., Biol., Phys. 67(1), 48-56 (2007).

R.T.O.G. 0415, "A Phase III Randomized Study of Hypofractionated 3D-CRT/IMRT Versus Conventionally Fractionated 3D-CRT/IMRT in patients with favourable-risk prostate cancer", (www.RTOG. orgaccessed on Jul. 2006) (2006).

Yan, D. et al., "The influence of interpatient and intrapatient rectum variation on external beam treatment of prostate cancer", Int. J. Radiat. Oncol., Biol., Phys. 51(4), 1111-1119 (2001).

Hoogeman, M.S. et al., "A model to simulate day-to-day variations in rectum shape", Int. J. Radiat. Oncol., Biol., Phys. 54(2), 615-625 (2002).

Jiang, Z. et al., "An examination of the number of required apertures for step-and-shoot- IMRT", Phys. Med. Biol. 50 (23), 5653-5663 (Nov. 24, 2005).

Godfrey, D.J. et al., "Digital tomosynthesis with an on-board kilovoltage imaging device", Int. J. Radiat. Oncol., Biol., Phys. 65(1), 8-15 (2006).

Mestrovic, A. et al., "Direct aperture optimization for online adaptive radiation therapy", Med. Phys. 34(5), Apr. 19, 2007.

International Search Report issued on PCT application No. PCT/CA2007/001339, mailed Dec. 13, 2007.

Bortfeld et al., "Clinically relevant intensity modulation optimization using physical criteria," In Proceedings of the XII International Conference on the Use of Computers in Radiation Therapy, Salt Lake City, Utah, 1-4 (1997).

Earl et al., "Inverse Planning for Intensity-Modulated Arc Therapy Using Direct Aperture Optimization", Physics in Medicine and Biology 48 (2003), Institute of Physics Publishing, pp. 1075-1089.

Spirou et al., "A Gradient Inverse Planning Algorithm with Dose-Volume Contraints", Med. Phys. 25, pp. 321-333 (1998).

Wu et al., "Algorithm and Functionality of an Intensity Modulated Radiotherapy Optimization System", Med. Phys. 27, pp. 701-711 (2000).

Spirou et al., "Generation of Arbitrary Intensity Profiles by Dynamic Jaws or Multileaf Collimators", Med. Phys. 21, pp. 1031-1041 (1994).

Xia et al., "Multileaf Collimator Leaf Sequencing Algorithm for Intensity Modulated Beams with Multiple Static Segments", Med. Phys. 25, pp. 1424-1434 (1998).

Otto et al., "Enhancement of IMRT Delivery through MLC Rotation", Phys. Med. Biol. 47, 3997-4017 (2002).

M.-P. Milette and K. Otto, "Maximizing the potential of direct aperture optimization through collimator rotation," Med. Phys. 34, 1431-1438 2007.

Tervo et al., "A Model for the Control of a Multileaf Collimator in Radiation Therapy Treatment Planning", Inverse Problems 16 (2000), pp. 1875-1895.

Shepard et al., "An Arc-Sequencing Algorithm for Intensity Modulated Arc Therapy", Med. Phys. 34 (2) (2007), pp. 464-470.

Cao et al., "Continuous Intensity Map Optimization (CIMO): A Novel Approach to Leaf Sequencing in Step and Shoot IMRT", Med. Phys. 33 (4) (2006), pp. 859-867.

Ulrich et al., "Development of an Optimization Concept for Arc-Modulated Cone Beam Therapy", Phys. Med. Biol. 52 (2007), pp. 4099-4119.

Hardemark et al., Direct Machine Parameter Optimization with RayMachine in Pinnacle, RaySearch White Paper, RaySearch Laboratories (2003).

C. X. Yu, "Intensity-modulated arc therapy with dynamic multileaf collimation: An alternative to tomotherapy," Phys. Med. Biol. 40, 1435-1449 1995.

A. Gladwish et al., "Segmentation and leaf sequencing for intensity modulated arc therapy," Med. Phys. 34, 1779-1788 2007.

E. Wong, J. Z. Chen, and J. Greenland, "Intensity-modulated arc therapy simplified," Int. J. Radiat. Oncol. Biol. Phys. 53, 222-235 2002.

K. Bratengeier, "2-Step IMAT and 2-Step IMRT in three dimensions," Med. Phys. 32, 3849-3861 2005.

C. Cameron, "Sweeping-window arc therapy: An implementation of rotational IMRT with automatic beam-weight calculation," Phys. Med. Biol. 50, 4317-4336 2005.

S. M. Crooks et al., "Aperture modulated arc therapy," Phys. Med. Biol. 48, 1333-1344 2003.

* cited by examiner

SYSTEMS AND METHODS FOR OPTIMIZATION OF ON-LINE ADAPTIVE RADIATION THERAPY

RELATED APPLICATIONS

This application claims priority from U.S. patent application No. 60/820,582 filed on 27 Jul. 2006, which is hereby incorporated herein by reference.

TECHNICAL FIELD

The invention relates to radiation therapy. Particular embodiments of the invention provide systems and methods for optimizing the delivery of radiation dose to an individual.

BACKGROUND

Radiation therapy is used for various medical applications, such as combating cancer, for example. Generally, speaking when irradiating a subject, it is desirable to impart a prescribed radiation dose to the diseased tissue (referred to as the "target" or "target volume"), while minimizing (to the extent possible) the dose imparted to surrounding healthy tissue and organs. Various systems and methods have been devised for delivering radiation while trying to achieve this objective. Such systems and methods generally involve: obtaining one or more images of a region of interest (including the target volume) in the subject's body; initializing a radiation treatment plan; adapting or optimizing radiation delivery variables in effort to achieve the objectives of the treatment plan; and delivering radiation. These procedures are illustrated in FIG. 1.

One drawback with current techniques is the time taken between the imaging procedure and completion of the radiation delivery procedure. The imaging procedure may involve obtaining a computed tomography (CT) image for example. The time between completing the imaging procedure and starting the radiation delivery procedure may typically be on the order of a week or two. Moreover, radiation delivery typically involves several discrete steps referred to as "fractions". By way of example, a treatment plan may be divided into 10 fractions and a subject may receive one fraction every day for 10 days. Thus, it may take on the order of several weeks to a month (or more) between the imaging procedure and completion of the radiation delivery procedure.

The characteristics of the target volume (e.g. the size, shape and/or location of the target volume) and the characteristics of the healthy tissue (e.g. the size, shape and/or location of the healthy tissue relative to the target volume) can change over time. By way of non-limiting example, a tumor in a subject's lung commonly moves whenever the subject moves and a tumor in a subject's prostate may be deformed by changes in the shape of the bladder and/or the rectum. Because the likelihood of changes in the characteristics of the target volume and/or the characteristics of the healthy tissue increases with time, the time between imaging and radiation delivery represents a significant limitation to the general desire of imparting a prescribed radiation dose to the target volume, while minimizing (to the extent possible) the dose imparted to surrounding healthy tissue and organs.

Newer radiation delivery systems and methods referred to as "on-line" adaptive radiation therapy (ART) have attempted to reduce this time between the imaging and radiation delivery procedures. In on-line ART techniques, each of the FIG. 1 procedures is implemented for each treatment fraction. That is, for each fraction (i.e. each time that the subject comes to the hospital), the subject is subjected to serially implemented imaging, initializing, optimizing and radiation delivery procedures. Because on-line ART techniques involve a separate imaging procedure (for each fraction) and radiation is delivered (for each fraction) relatively soon after imaging, the characteristics of the target volume and the healthy tissue are less likely to change between the imaging and radiation delivery procedures of each fraction. Accordingly, on-line ART has achieved some success at addressing the general desire of imparting a prescribed radiation dose to the target volume, while minimizing (to the extent possible) the dose imparted to surrounding healthy tissue and organs.

These gains achieved by on-line ART have not come without cost. For on-line ART, the subject is typically required to be stationary on the treatment couch (or at least in the treatment facility under the care of medical staff) for the entirety of each fraction (i.e. for each iteration of the imaging, initializing, optimizing and radiation delivery procedures). Accordingly, current on-line ART techniques are expensive to implement because it takes a relatively long time to implement each fraction. Treatment of each subject using on-line ART occupies the radiation delivery system and other hospital resources (e.g. medical staff, rooms etc.) for a relatively large amount of time. In addition, the subject is required, for each fraction, to spend a relatively long time at the treatment facility which is generally undesirable.

There is a general desire to reduce the amount of time required for each iteration (i.e. each fraction) of on-line ART techniques.

SUMMARY

Aspects of the present invention provide methods and systems for radiation treatment.

One aspect of the invention provides a method for radiation treatment of a subject involving one or more fractional treatments. A fractional treatment comprises: obtaining fractional image data pertaining to a region of interest of the subject; performing a fractional optimization of a radiation treatment plan to determine optimized values of one or more radiation delivery variables based at least in part on the fractional image data; and delivering a fraction of the radiation treatment plan to the region of interest using the optimized values of the one or more radiation delivery variables as one or more corresponding parameters of the radiation treatment plan. A portion of performing the fractional optimization overlaps temporally with a portion of at least one of: obtaining the fractional image data and delivering the fraction of the radiation treatment plan.

Another aspect of the invention provides a method for radiation treatment of a subject involving one or more fractional treatments. The method involves obtaining initial image data pertaining to a region of interest of the subject and performing initial optimization of an initial radiation treatment plan to determine optimized initial values of one or more initial variables based at least in part on the initial image data. For at least one fractional treatment the method comprises: obtaining fractional image data pertaining to the region of interest of the subject; performing a fractional optimization of a radiation treatment plan to determine optimized values of one or more radiation delivery variables based at least in part on the fractional image data; and delivering a fraction of the radiation treatment plan to the region of interest using the optimized values of the one or more radiation delivery variables as one or more corresponding parameters of the radiation treatment plan. Performing the initial optimization comprises using a first optimization technique and performing the fractional optimization comprises using a second optimization technique. The first and second optimization techniques differ from one another.

Other aspects of the invention provide computer program products and systems for implementing the inventive methods disclosed herein.

Further aspects of the invention, features of specific embodiments of the invention and applications of the invention are described below.

BRIEF DESCRIPTION OF THE DRAWINGS

In drawings which depict non-limiting embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Aspects of the invention provide methods for radiation treatment of a subject involving one or more fractional treatments. In accordance with particular embodiments, a fractional treatment comprises: obtaining fractional image data pertaining to a region of interest of the subject; performing a fractional optimization of a radiation treatment plan to determine optimized values of one or more radiation delivery variables based at least in part on the fractional image data; and delivering a fraction of the radiation treatment plan to the region of interest using the optimized values of the one or more radiation delivery variables as one or more corresponding parameters of the radiation treatment plan. A portion of performing the fractional optimization may overlap temporally with a portion of either or both of: obtaining the fractional image data and delivering the fraction of the radiation treatment plan. The methods may involve performing an initial optimization based on initial image data. The initial optimization may use a different optimization technique than the fractional optimization.

Figure 1:
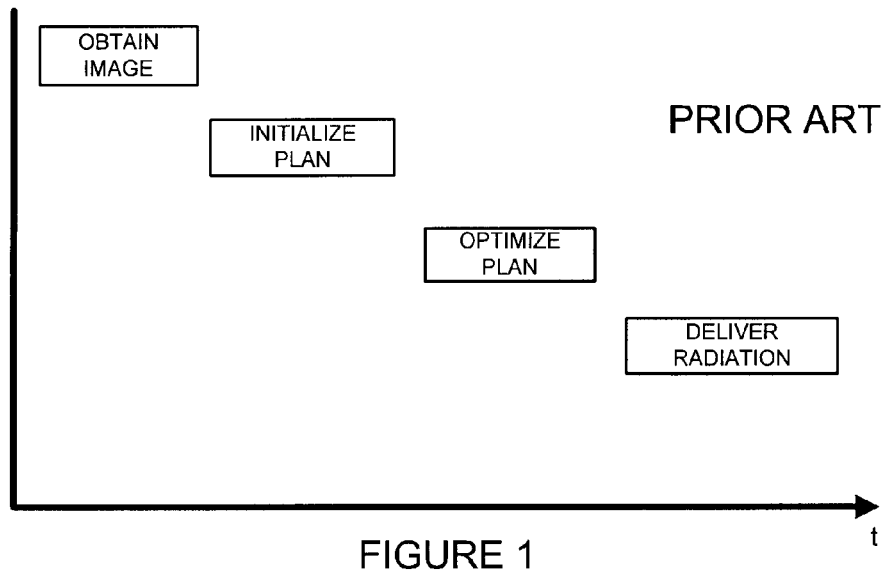
FIG. 1 is a Gantt-type temporal plot showing the procedures involved in a typical prior art radiation treatment technique.
Figure 2:
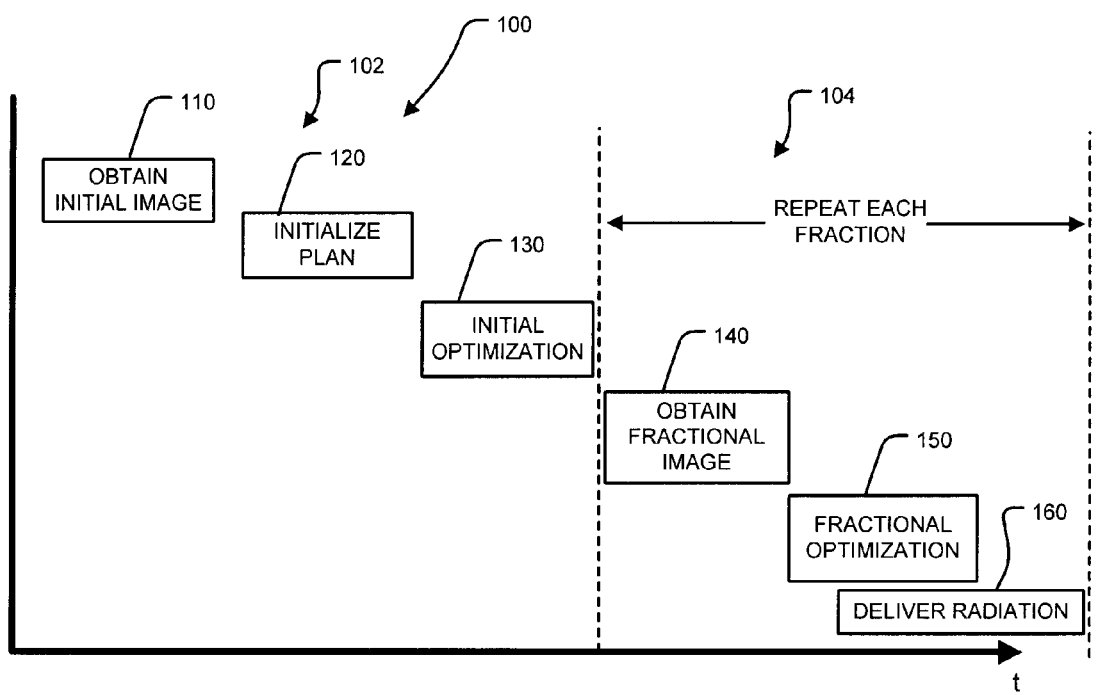
FIG. 2 is a Gantt-type temporal plot showing the timing of the procedures involved in a method for radiation treatment according to a particular embodiment of the invention.

FIG. 2 is a temporal chart which schematically illustrates the timing of the procedures involved in radiation treatment method 100 according to a particular embodiment of the invention. As illustrated in FIG. 2, radiation treatment method 100 may generally be divided into a plan initialization process 102 and a fractional process 104. Plan initialization process 102 is performed once per subject to be irradiated. Fractional process 104 is performed once for each fraction (i.e. fractional process 104 may be performed a plurality of times to complete a radiation treatment).

Plan initialization process 102 of radiation treatment method 100 starts in block 110 which involves obtaining an initial image of a region of interest of the subject. Typically, although not necessarily, a subject will visit a treatment facility so that the block 110 initial image may be obtained from the subject. The region of interest imaged in block 110 may include the target volume and the surrounding tissue. The block 110 procedure for obtaining the initial image may be substantially similar to prior art imaging procedures and may be accomplished using any suitable imaging equipment and procedures. Preferably, the block 110 initial image is obtained using a three-dimensional imaging technique. By way of non-limiting example, the block 110 initial image may be obtained using conventional CT scanning, cone-beam CT scanning, magnetic resonance imaging (MRI), positron emission tomography (PET), ultrasound imaging, tomosynthesis or the like.

Once the block 110 initial image is obtained, the radiation treatment plan is initialized in block 120. The subject need not be present at the treatment facility for the block 120 treatment plan initialization. The block 120 treatment plan initialization may be accomplished using procedures substantially similar to prior art techniques for initializing radiation treatment plans. In the illustrated embodiment, the block 120 treatment plan initialization comprises determining a set of treatment plan objectives and initializing the parameters of the treatment plan. The parameters of a treatment plan may comprise a number of fixed parameters and a number of variable parameters. The block 120 treatment plan initialization may be based on information obtained from the block 110 initial image. The objectives of a radiation treatment plan may be prescribed by medical professionals and may specify desired dose levels (or a range of desired dose levels) to be delivered to the target volume and maximum desired dose levels to be delivered to surrounding tissue and organs.

A non-limiting example of a set of radiation treatment plan objectives is shown in Table 1. The Table 1 treatment plan objectives are derived from the RTOG Prostate IMRT Protocol for providing radiation treatment to a cancerous target volume located in the subject's prostate.

TABLE 1

Treatment Plan Objectives

| Non-Target Organ Objectives | No more than 15% vol. receives dose that exceeds | No more than 25% vol. receives dose that exceeds | No more than 35% vol. receives dose that exceeds | No more than 50% vol. receives dose that exceeds |
|---|---|---|---|---|
| Bladder | 80 Gy | 75 Gy | 70 Gy | 65 Gy |
| Rectum | 75 Gy | 70 Gy | 65 Gy | 60 Gy |

| Target Objectives | Minimum Target Volume Dose (over more than 98% of target vol.) | Maximum Target Volume Dose |
|---|---|---|
| Planning Treatment Volume (Target Volume) | 73.8 Gy | 79 Gy |

The Table 1 treatment plan objectives represent one particular set of treatment plan objectives for one particular treatment. It will be appreciated by those skilled in the art that treatment plan objectives may generally differ from those of Table 1. In some embodiments, a treatment plan will specify a maximum dose to be delivered to a "shell". A shell typically surrounds the target volume, but may not contain any important healthy organs. The dose delivery maximum for a shell may be included in the treatment plan objectives to eliminate "hot spots" which may be outside of the target volume and which may not part of the Non-Target Organ Objective specified by the plan objectives.

Treatment plan objectives may optionally involve truncation of the volume of the non-target organs or some other procedure for removing portions of the volume of the non-target organs from consideration. For example, when treating the prostate, portion(s) of the bladder and/or portion(s) of the rectum may be located sufficiently far from the target volume such that these portion(s) would receive negligible dose. In such cases, it may be desirable to remove these portion(s) from consideration in the treatment plan. The removal of volume from non-target organs may make it more difficult to achieve the treatment plan objectives, as the maximum dose limits for the non-target organs represent a percentage of a smaller volume.

Initializing the treatment plan parameters as part of the block 120 initialization may depend on the available radiation treatment equipment (not explicitly shown in FIG. 2) and the types of radiation delivery plans suitable for use with such radiation treatment equipment. In some embodiments of the invention, the radiation treatment plan used in method 100 comprises a plan suitable for use with direct aperture optimization (DAO) radiation treatment.

DAO radiation treatment typically involves movement of a radiation source to a number of discrete locations (e.g. around a subject) and then directing one or more beams at the subject from each such discrete location. Each individual location of the radiation source relative to the subject results in a different beam orientation. The orientations of the beams relative to the subject and the number of beams directed toward the subject in each orientation may be referred to as the "beam arrangement" of the treatment plan. The beam arrangement characteristics represent parameters of a DAO radiation treatment plan. The block 120 treatment plan initialization may involve determining the characteristics of the beam arrangement (i.e. the orientations of the beams relative to the subject and the number of beams directed toward the subject in each orientation).

Figure 3:
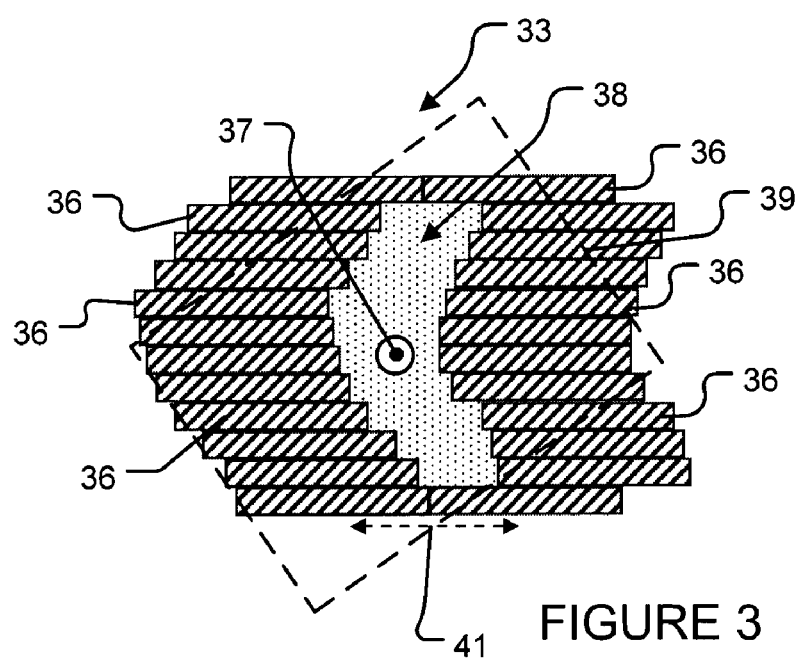
FIG. 3 is a schematic plan view of a multi-leaf collimator suitable for use in implementing the method of FIG. 2.

In DAO systems, the cross-sectional shape of each beam directed toward the patient may be controlled by a multi-leaf collimator (MLC) or some other suitable beam-shaping device. A typical MLC 33 is shown schematically in FIG. 3 and comprises a plurality of opposing pairs of collimator leaves 36. Collimator leaves 36 (which may be fabricated from material that is at least partially impermeable to radiation) are individually movable in the directions of double-headed arrow 41 to control the shape of one or more openings(s) 38 and to thereby control the cross-section of the beam. As shown in dashed lines, MLC 33 may also be pivotable about axis 37, which, in the FIG. 3 illustration, extends into and out of the page. Pivotal motion about axis 37 permits further adjustment of the cross-section of the beam. Because MLC 33 controls aperture 38 which in turn determines the cross-section of the individual beams in DAO systems, the individual beams in a DAO radiation treatment system are often referred to in the art as "apertures". In addition to controlling the cross-section of each beam, DAO treatment systems typically control the quantity or "weight" of the radiation beam that passes through MLC 33 and impinges on the subject.

The beam apertures (as controlled by the MLC leaf positions and, optionally, the MLC orientation) and the beam weights represent other DAO treatment plan parameters which may be initialized in block 120. In some embodiments, the MLC leaf positions and orientations are initialized in block 120 such that the shapes of the resultant beams match a projection of the target volume (e.g. to approximate a beam's eye view outline of the target volume) and the beam weights are initialized in block 120 to have equal values which may be set so that the mean dose in the target volume will equal a prescribed dose objective.

After initializing a plan in block 120, method 100 proceeds to block 130 which involves optimizing the one or more of the treatment plan parameters in effort to achieve the plan objectives. The subject need not be present at the treatment facility for the block 130 initial optimization. In some embodiments, the block 130 initial optimization may be performed in accordance with procedures substantially similar to prior art techniques for optimizing radiation treatment plan parameters in effort to meet treatment plan objectives. In other embodiments, the block 130 initial optimization may differ from prior art optimization techniques. Optimizing treatment plan parameters in effort to meet the plan objectives typically involves adjusting various treatment plan parameters in an attempt to minimize (at least to an acceptable level) a cost function (also referred to as an objective function).

Typically, a cost function is constructed on the basis of the treatment plan objectives and may provide a metric of plan quality based on how a given plan is expected to meet the plan objectives. A typical cost function combines an expression that reflects the target volume and an expression that reflects the surrounding tissue. The cost function may increase when the radiation delivered to the target volume is below a certain minimum target threshold and/or when the radiation delivered to the target volume is above a certain maximum target threshold and may decrease when the radiation delivered to the target volume is between the minimum and maximum target thresholds. The cost function may increase when the radiation delivered to certain regions of the surrounding tissue (e.g. tissue corresponding to important non-target organs) is above a minimum non-target threshold. Various aspects of the cost function may be weighted differently than others.

In one non-limiting example, a quadratic cost function is provided which includes a set of terms for the target volume and one set of terms for the critical non-target structures (e.g. non-target organs). For the target, the minimum and the maximum allowed dose ($D_{min}$ and $D_{max}$) are specified together with the respective weights ($w_t^{min}$ and $w_t^{max}$) and the target terms of the cost function are given by:

$$F_t = \frac{w_t^{min}}{N_t} \sum_{i=1}^{N_t} (D_i - D_{min})^2 H(D_{min} - D_i) + \frac{w_t^{max}}{N_t} \sum_{i=1}^{N_t} (D_i - D_{max})^2 H(D_i - D_{max}) \quad (1)$$

where $H(x)$ is a step function given by:

$$H(x) = \begin{Bmatrix} 1 & x \geq 0 \\ 0 & x < 0 \end{Bmatrix} \quad (2)$$

For each critical non-target structure (e.g. non-target organ), the volume receiving a dose greater than $D_1$ should be less than $V_1$. One technique for implementing this condition is described by Bortfeld et al. (*Clinically relevant intensity modulation optimization using physical criteria*. In Proceedings of the XII International Conference on the Use of Computers in Radiation Therapy, Salt Lake City, Utah, 1997:1-4.) and involves defining another dose $D_2$ such that the volume that receives the dose $D_2$ is $V_1$. The critical structure dose volume term of the cost function is then given by:

$$F_{OAR} = \frac{w_{OAR}}{N_{OAR}} \sum_{i=1}^{N} (D_i - D_1)^2 \cdot H(D_i - D_1) \cdot H(D_2 - D_i) \quad (3)$$

Equation (3) ensures that only voxels receiving dose between $D_1$ and $D_2$ are penalized in the cost function. For each critical structure, an unlimited number of dose-volume conditions can be specified.

Block 130 involves varying treatment plan parameters in effort to minimize the cost function. The particular treatment plan parameters that are varied during optimization are referred to herein as "radiation delivery variables". As discussed above, in a DAO radiation treatment system, the radiation treatment plan parameters include, without limitation: the characteristics of the beam arrangement (e.g. the orientations of the beams and the number of beams directed toward the subject in each orientation); the positions of the MLC leaves 36 for each beam; the orientation of MLC 33 about axis 37 for each beam; and the weight of each beam. In particular embodiments, treatment plan parameters used as radiation delivery variables during the block 130 initial optimization are limited to: the positions of the MLC leaves 36 for each beam and the weight of each beam. This limitation is not necessary. Optionally, DAO optimizations (including the block 130 initial optimization and the block 150 fractional optimization discussed in more detail below) may involve variation of other treatment plan parameters, such as the pivotal orientation of MLC 33 about axis 37, various characteristics of the beam arrangement or the like. The remainder of this description assumes, unless otherwise stated, that the radiation delivery variables include only the positions of the MLC leaves 36 for each beam and the weight of each beam. This assumption is made without loss of generality and is made for the purpose of simplifying explanation only.

In particular radiation treatment plans, the radiation delivery variables take on different values at different control points. Each radiation treatment plan may comprise a number of control points. Control points may (but need not necessarily) correspond to fixed parameters of a radiation treatment plan. For example, in some embodiments, the control points of a DAO radiation treatment plan correspond to the individual beams of the beam arrangement. In such embodiments, the radiation delivery variables (e.g. the positions of the MLC leaves 36 and the beam weight) may be different for each of the individual beams of the beam arrangement.

The block 130 optimization process involves optimizing the radiation delivery variables in effort to minimize the cost function. In one particular embodiment, the block 130 optimization involves iteratively: selecting and modifying one or more radiation delivery variable(s); evaluating the quality of the dose distribution resulting from the modified optimization variable(s)—e.g. by computing the cost function; and then making a decision to accept or reject the modified radiation delivery variable(s).

Typically, although not necessarily, the block 130 optimization will be subject to a number of constraints. In some embodiments, such constraints may reflect various physical limitations of the radiation treatment system (e.g. a range of acceptable positions for MLC leaves 36 and/or a range of acceptable beam intensities). In some embodiments, these optimization constraints may be determined by image information obtained in block 110. For example, it may be desirable to constrain the range of the MLC leaves 36 such that the cross-sectional shape of each beam does not exceed the beam's eye view projection of the target volume. In some embodiments, the block 130 constraints are related to the amount of change in one or more radiation delivery variables that may be permitted between successive optimization iterations (e.g. a maximum change of MLC leaf position between successive optimization iterations).

It will be appreciated by those skilled in the art, that the block 130 optimization may generally be accomplished using any suitable optimization technique. Non-limiting examples of suitable optimization techniques include: Nelder-Mead method optimization (the Amoeba method), gradient method optimization, subgradient method optimization, simplex method optimization, ellipsoid method optimization, simulated annealing optimization, quantum annealing optimization, stochastic tunneling optimization, genetic optimization algorithms or the like. The block 130 optimization may also involve variations and combinations of these optimization techniques.

The conclusion of the block 130 initial optimization marks the end of plan initialization process 102. At the conclusion of plan initialization process 102, method 100 has access to an initial optimized radiation treatment plan. The initial optimized radiation plan includes a set of initial radiation delivery variables which is optimized for delivery of radiation to the subject based on the initial image obtained in block 110.

Method 100 then enters its first fractional process 104. As mentioned above, fractional process 104 may be implemented once for each fraction of radiation treatment method 100. It is generally preferable (although not necessary) for the subject to remain present at the treatment facility for each iteration of fractional process 104. In some embodiments, the subject can remain on the treatment "couch" for the duration of each fractional process 104.

Fractional process 104 commences in block 140 which involves obtaining an updated image of the region of interest. This block 140 updated image may be referred to as a "fractional image". Like the block 110 initial image, the region of interest for the block 140 fractional image may include the target volume and the surrounding tissue. In general, the block 140 fractional image may be obtained using any suitable imaging technique, including any of the imaging techniques discussed herein for block 110. However, the block 140 fractional image need not be obtained using the same imaging technique as the block 110 initial image. In particular embodiments, the block 140 fractional image is obtained according to a tomosynthesis imaging technique which has a relatively short image acquisition time and a relatively short image reconstruction time.

The block 140 fractional image is obtained at a time proximate to the delivery of a fractional radiation dose (when compared to the block 110 initial image. Also, the subject may remain in one general position between the block 140 fractional image and the block 160 fractional radiation delivery discussed further below. Consequently, the block 140 fractional image represents a more accurate (e.g. more current) representation of the region of interest than the block 110 initial image. By way of non-limiting example, the block 140 fractional image may account for changes in shape or size of the target volume, movement of the target volume, changes in shape or size of neighboring tissue/organs or the like which may have occurred between the time of the block 110 initial image and the block 140 fractional image.

In the FIG. 2 embodiment, once a fractional image is obtained in block 140, method 100 proceeds to block 150 which involves further optimizing the radiation delivery variables to account for new information obtained from the block 140 fractional image. In the first iteration of fractional process 104, the block 150 fractional optimization may involve further optimizing radiation treatment plan of plan initialization process 102 (i.e. the output of block 130). That is, the first iteration of the block 150 fractional optimization may involve initializing the treatment plan parameters with the parameters of the block 130 initial optimized radiation treatment plan and then further optimizing the radiation delivery variables to account for the new information obtained in the block 140 fractional image. In subsequent iterations of fractional process 104, the block 150 fractional optimization may involve further optimizing the radiation treatment plan of plan initialization process 102 or the block 150 fractional optimization may involve further optimizing the radiation treatment plan of the previous block 150 optimization.

The output of block 150 is a further optimized radiation treatment plan (including a further optimized set of radiation delivery variables) that incorporates the changes in the subject's region of interest which may have occurred between the block 110 initial image and the block 140 fractional image processes. Since the block 150 fractional optimization accounts for these potential changes to the subject's region of interest, the resultant further optimized radiation treatment plan helps to achieve the general desire of imparting a prescribed radiation dose to the target volume, while minimizing (to the extent possible) the dose imparted to surrounding healthy tissue and organs.

The block 150 fractional optimization may differ from the block 130 initial optimization. Preferably, the block 150 fractional optimization takes less time than the block 130 initial optimization. In particular embodiments, the block 150 fractional optimization takes less than 10 minutes. In preferred embodiments, the block 150 fractional optimization process takes less than 5 minutes. The relatively short fractional optimization process of block 150 helps to achieve the desire of reducing the amount of time required for each fraction.

In particular embodiments, it is assumed that the changes in the subject's region of interest between the block 110 initial image and the block 140 fractional image processes are relatively minor. This assumption leads to the corresponding assumption that the block 150 fractional optimization should obtain a result (i.e. a further optimized set of radiation delivery variables) that is relatively close to its initial set of radiation delivery variables. As discussed above, the initial set of radiation delivery variables for the block 150 fractional optimization may include those of the radiation treatment plan determined in plan initialization process 102 or those of the previous iteration of block 150. As discussed in more detail below, these assumptions permit the use of several time-saving procedures for the block 150 fractional optimization which would not be suitable or possible for use with the block 130 initial optimization.

Fractional process 104 also involves delivering radiation in block 160. The block 160 fractional radiation delivery comprises delivering a particular fraction of the radiation treatment plan in accordance with the further optimized set of radiation delivery variables determined in the block 150 fractional optimization. As shown in FIG. 2, the block 160 fractional radiation delivery procedure may commence prior to completion of the block 150 fractional optimization—i.e. a portion of the block 150 fractional optimization and a portion of the block 160 fractional radiation delivery may occur simultaneously. The ability to commence the block 160 radiation delivery prior to completion of the block 150 fractional optimization may also be based on the assumption that the changes in the subject's region of interest between the block 110 initial image and the block 140 fractional image processes are relatively minor.

In one embodiment, the block 150 fractional optimization procedure comprises cycling through all of the individual beams (i.e. apertures) in the beam arrangement and optimizing the radiation delivery variables of each beam (e.g. the MLC leaf positions and beam weight) as it cycles through the beams. However, instead of continually cycling through all of the beams until the radiation delivery variables are completely optimized (at least to a clinically acceptable level), the block 150 optimization may be performed for a period $T_1$. The period $T_1$ may comprise a threshold number of optimization iterations, a threshold time, achievement of a threshold level for the cost function, achievement of a threshold rate of change of the cost function between iterations or the like.

After the period $T_1$, the radiation delivery variables of a first beam may be fixed. The first beam of the block 160 radiation delivery may be permitted to commence as soon as the radiation delivery variables of the first beam are fixed (i.e. after the period $T_1$). Once the radiation delivery variables of the first beam are fixed, the first beam is removed from the block 150 fractional optimization and the block 150 fractional optimization continues to optimize the radiation delivery variables of the remaining beams while radiation is being delivered in the first beam. After continuing to optimize the remaining beams for a second period $T_2$, the radiation delivery variables of a second beam are fixed, whereupon the second beam of the block 160 radiation delivery may be permitted to commence and the block 150 optimization can remove the second beam from the optimization process and continue optimizing for the remaining available beams. This procedure can be repeated until the block 150 fractional optimization is completed with the final beam. As discussed in more detail below, the optimization of particular beams and the random variables for each such beam may (but need not necessarily) proceed in a particular order to facilitate the overlap of the block 160 radiation delivery and the block 150 fractional optimization.

Figure 5:
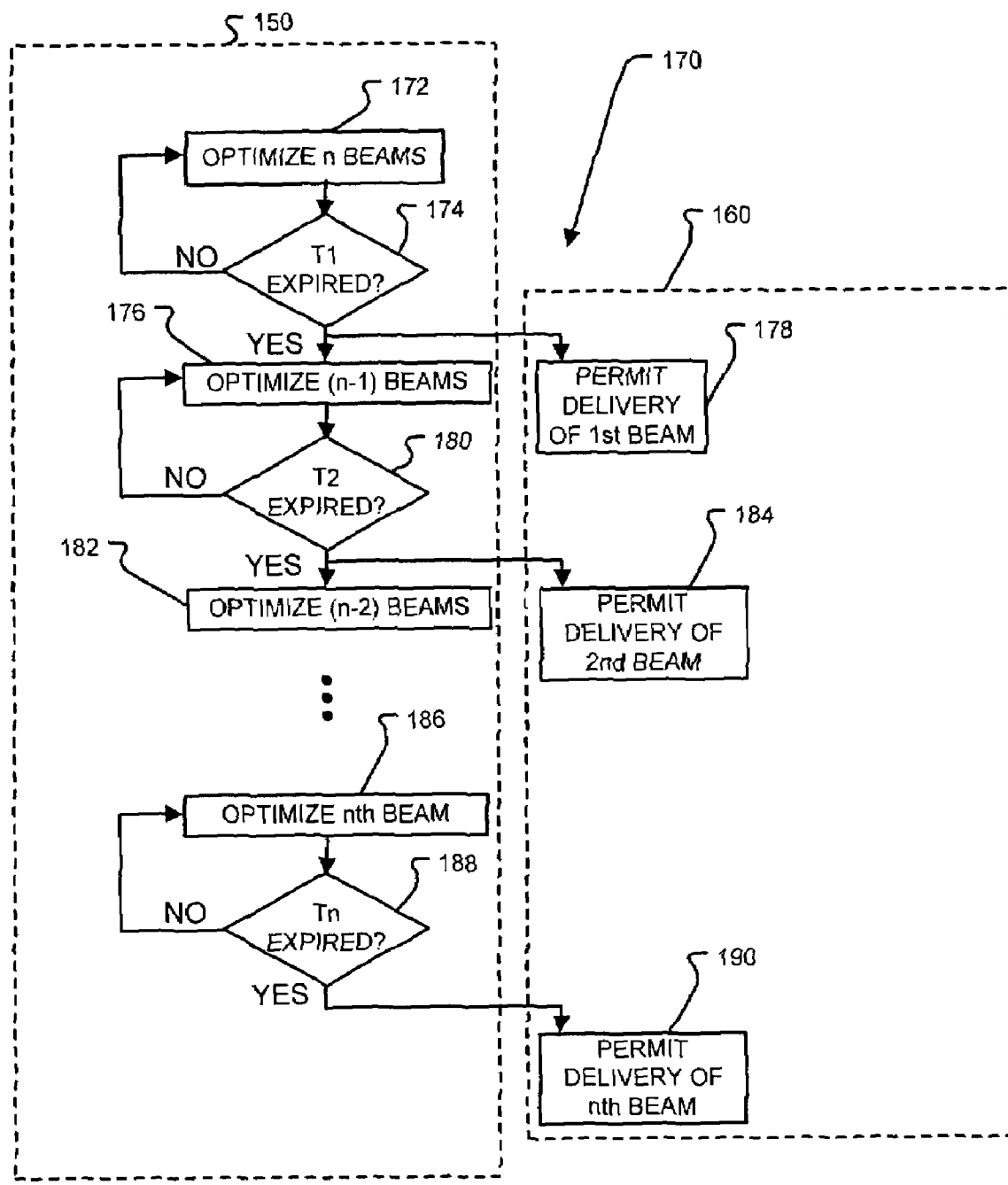
FIG. 5 is a schematic description of the optimization and radiation delivery procedures of the FIG. 2 method according to a particular embodiment of the invention.

This procedure for commencing the block 160 fractional radiation delivery prior to the completion of the block 150 fractional optimization is schematically depicted in method 170 of FIG. 5. Method 170 commences in block 172 which involves optimizing the radiation delivery variables for all of the beams in the beam arrangement of the radiation delivery plan. In the illustrated embodiment, it is assumed that the total number of beams in the beam arrangement is n. Block 174 involves evaluating whether the period $T_1$ has expired. If the period $T_1$ has not expired (block 174 NO output), then method 170 returns to block 172 and continues optimizing the radiation delivery variables for all n beams.

If, on the other hand, the period $T_1$ has expired (block 174 YES output), then method 170 permits delivery of the first beam of radiation in block 178. Simultaneously, method 170 proceeds to block 176, where the first beam is removed from the block 150 optimization process and the block 150 optimization process continues optimizing the remaining n−1 beams. When $T_2$ has expired (block 180 YES output), method 170 permits delivery of the second beam of radiation in block 184 and simultaneously proceeds to block 182, where the second beam is removed from the block 150 optimization process and the block 150 optimization process continues optimizing the remaining n−2 beams. This process may continue until block 186, which involves optimizing the radiation delivery variables for the last ($n^{th}$) beam. When the last period ($T_n$) expires (block 188 YES output), method 170 permits delivery of the last ($n^{th}$) beam in block 190 and is completed.

While the periods $T_1, T_2, \ldots$ may be the same for each iteration, this is not generally necessary. Preferably, to achieve a high efficiency, the temporal duration of the periods $T_1, T_2, \ldots$ is less than the time required to deliver the radiation for a particular beam. That is, preferably the block 150 fractional optimization for a particular beam takes less time than the block 160 delivery of radiation for the preceding beam. With this high efficiency condition, beams will be able to be delivered as soon as they are permitted to be delivered and there will be no "dead time" between the block 160 delivery radiation for successive beams. Again, however, this high efficiency condition is not necessary, as there will still be efficiency gains for any overlap of the block 150 fractional optimization and the block 160 radiation delivery.

The first iteration of fractional process 104 concludes at the end of the block 160 radiation delivery. Fractional process 104 may be repeated as many times as is desirable to achieve the radiation treatment plan. In some embodiments, each fraction is designed to deliver a corresponding fractional amount of the desired dose as set out in the radiation treatment plan objectives. That is, if there are ten fractions in the treatment plan, then each fraction is configured to deliver 1/10 of the prescribed dose. In other embodiments, the radiation treatment plan may be updated after each fractional delivery to account more precisely for the radiation actually delivered during a particular fraction. This treatment plan updating is not explicitly shown in method 100 of FIG. 2. However, in some embodiments, such treatment plan updating could occur between each iteration of fractional process 104 so that it could be done without requiring the patient to be present at the treatment facility. In other embodiments, this treatment plan updating could be done after each fractional imaging procedure 140.

Figure 4:
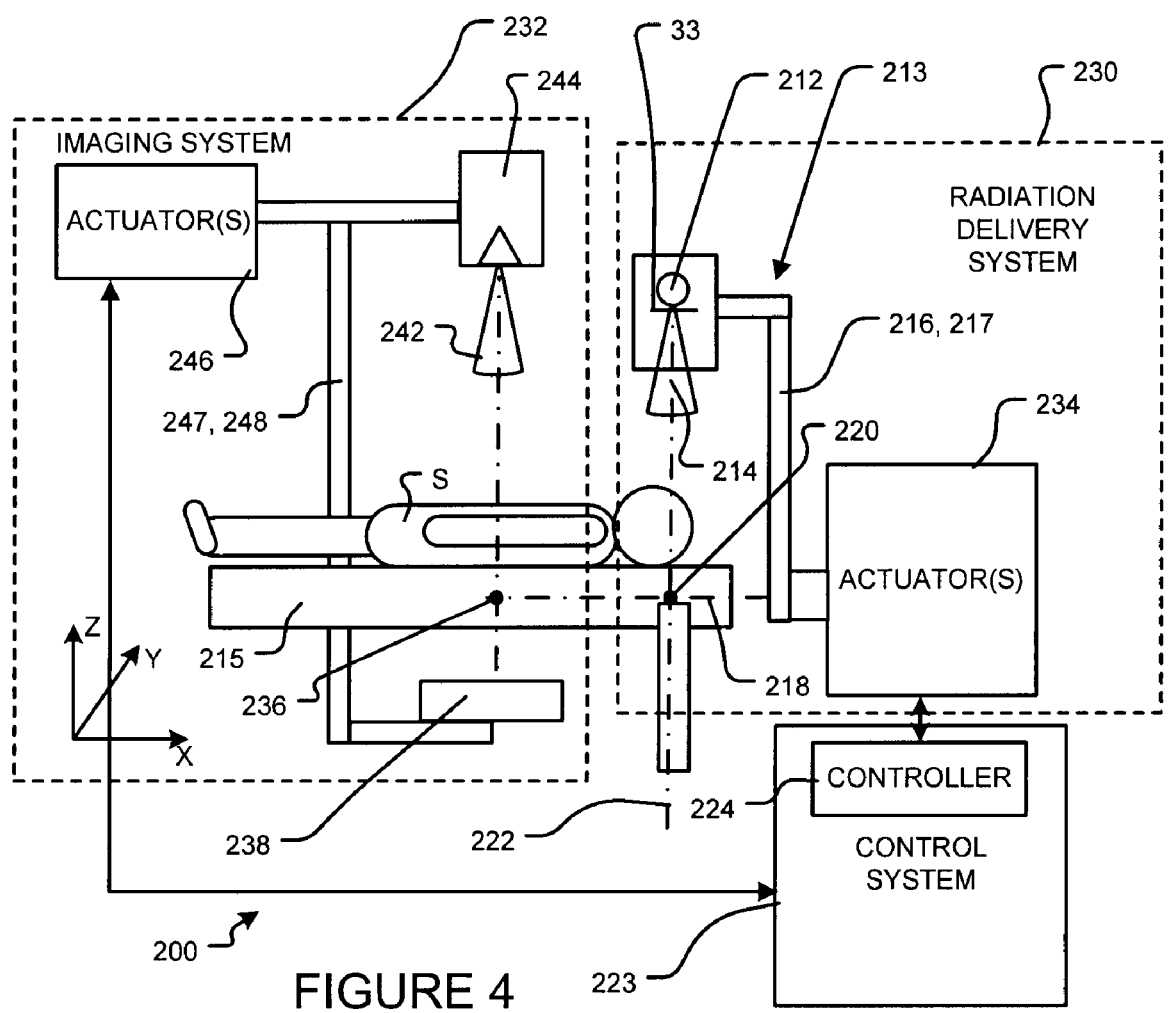
FIG. 4 is a schematic depiction of a radiation treatment system suitable for implementing the method of FIG. 2 according to a particular embodiment of the invention.

FIG. 4 depicts a radiation treatment system 200 according to a particular embodiment of the invention which may be suitable for performing radiation treatment method 100. Radiation treatment system 200 comprises a radiation source 212 capable of generating or otherwise emitting a beam 214 of radiation for treatment of subject S. Radiation source 212 may comprise a linear accelerator, for example. As discussed above, radiation treatment system 200 may comprise a beam-shaping device 33 for controlling the shape of beam 214. Beam-shaping device 33 may comprise a multi-leaf collimator, for example.

During fractional process 104 of method 100, subject S may be positioned on a table or "couch" 215 which can be placed in the path of beam 214. System 200 comprises one or more actuators 234 and movable parts 216 that permit the location of radiation source 212 and orientation of radiation beam 214 to be moved relative to subject S. Actuators 234 and movable parts 216 may be referred to collectively as a beam positioning mechanism 213. Beam positioning mechanism 213 together with radiation source 212 may be referred to as a radiation delivery system 230. Radiation delivery system 230 provides the radiation used to treat subject S.

Beam positioning system 213 may function to provide the various beam orientations of a DAO radiation delivery plan. In the illustrated system 200, movable parts 216 of beam positioning mechanism 213 comprises a gantry 217 which supports radiation source 212 and which can be rotated about an axis 218. Axis 218 and beam 214 intersect at an isocenter 220. Beam positioning mechanism 213 may also comprise a movable couch 215. In exemplary system 200, couch 215 can be translated in any of three orthogonal directions (shown in FIG. 3 as X, Y, and Z directions) and can be rotated about an axis 222. In some embodiments, couch 215 can be rotated about one or more of its other axes. The location of source 212 and the orientation of beam 214 can be changed (relative to subject S) by moving one or more of movable parts 216 of beam positioning mechanism 213.

In the illustrated embodiment, radiation treatment system 200 comprises an imaging system 232. Imaging system 232 may be used for the block 140 fractional imaging process and, optionally, for the block 110 initial imaging process. In the illustrated embodiment, imaging system 232 comprises a cone-beam CT imaging apparatus. As discussed above, a variety of other imaging apparatus (e.g. conventional CT scanning, cone-beam CT scanning, magnetic resonance imaging (MRI), positron emission tomography (PET), ultrasound imaging, tomosynthesis or the like) may be suitable for implementing radiation delivery method 100 and radiation treatment system 200 may generally incorporate any such imaging apparatus. Exemplary cone-beam CT imaging system 232 comprises an X-ray source 244 capable of generating or otherwise emitting an imaging X-ray beam 242. X-ray source 244 may comprise one or more beam-shaping devices (not explicitly shown) for controlling the shape of imaging beam 242.

Subject S may also be positioned on couch 215 during the block 140 fractional imaging process and, optionally, for the block 110 initial imaging process. Couch 215 may be placed in the path of imaging beam 242. The cone-beam CT imaging system 232 of the illustrated embodiment also comprises a detector unit 238 located on the opposing side of couch 215 from X-ray source 244. Detector unit 238 comprises one or more sensors that are sensitive to imaging beam 242. Imaging system 200 may comprise one or more actuators 246 and movable parts 247 that permit the location of X-ray source 244, the orientation of imaging beam 242 and the location of detector unit 238 to be moved relative to subject S.

In exemplary cone-beam CT imaging system 232, movable parts 247 comprises a gantry 248 which supports X-ray source 244 and detector unit 238 on opposing sides of couch 215. In the illustrated embodiment, gantry 248 of imaging system 232 is rotatable about axis 218 (i.e. the same axis about which gantry 217 of radiation delivery system 230 is capable of rotating). However, this is not necessary. In general, movable parts 247 may rotate X-ray source 244 and detector unit 238 about a different axis.

In the illustrated embodiment, axis 218 and imaging beam 242 intersect at an isocenter 236. It may be desirable that isocenter 236 of imaging system 232 be located at a particular location within subject S for the block 140 fractional imaging process. For example, it may be desirable that isocenter 236 be located within (or in close proximity) to the target volume in subject S. In particular embodiments, it may be desirable for isocenter 220 of radiation delivery system 230 be positionable at the same location (or at least within a threshold vicinity of the same location) during the block 160 fractional radiation delivery. In the illustrated embodiment of system 200, this common isocenter location may be implemented by moving couch 215 in the x direction between the block 140 fractional imaging process and the block 160 fractional radiation delivery, for example. In other embodiments, system 200 may be constructed such that the isocenters 220, 236 of radiation delivery system 230 and imaging system 232 are always coincident (or within a threshold proximity to one another). For example, X-ray source 244, detector unit 238 and radiation source 212 may be mounted on a single rotational gantry system. In one particular embodiment, X-ray source 244, detector unit 238 and radiation source 212 are mounted on a single rotational gantry such that imaging beam 242 is orthogonal to treatment radiation beam 214.

Radiation treatment system 200 comprises a control system 223. Control system 223 may be configured to control: the relative positions of the components of beam positioning mechanism 213; various other characteristics of radiation delivery system 230 (e.g. the intensity output of radiation source 212 and the characteristics of beam-shaping device 33); and the operation (including movement and image processing) of imaging system 232.

In the illustrated embodiment, control system 223 is schematically illustrated as a single unit. This is not necessary. Control system 223 may be distributed. For example, control system 223 may comprise separate control subsystems for controlling beam positioning mechanism 213, radiation delivery system 230 and/or imaging system 232. Control system 223 may generally comprise hardware components and/or software components. Control system 223 may comprise one or more data processors, together with suitable hardware, including, by way of non-limiting example: accessible memory, logic circuitry, drivers, amplifiers, A/D and D/A converters and like. Such data processors may comprise, without limitation, a microprocessor, a computer-on-a-chip, the CPU of a computer or any other suitable microcontroller. Control system 223 may comprise a plurality of data processors.

Control system 223 may be programmed with software or may otherwise have access to software (e.g. a program product or the like) which, when executed, may cause control system 223 to implement method 100 discussed above and method 300 discussed below.

As mentioned briefly above, in particular embodiments it may assumed that the changes in the subject's region of interest between the block 110 initial image and the block 140 fractional image processes are relatively minor which leads to the corresponding assumption that the block 150 fractional optimization should obtain a result (i.e. a further optimized set of radiation delivery variables) that is relatively close to its initial set of radiation delivery variables. These assumptions are schematically illustrated in FIG. 6.

Figures 6A, 6B, 6C:
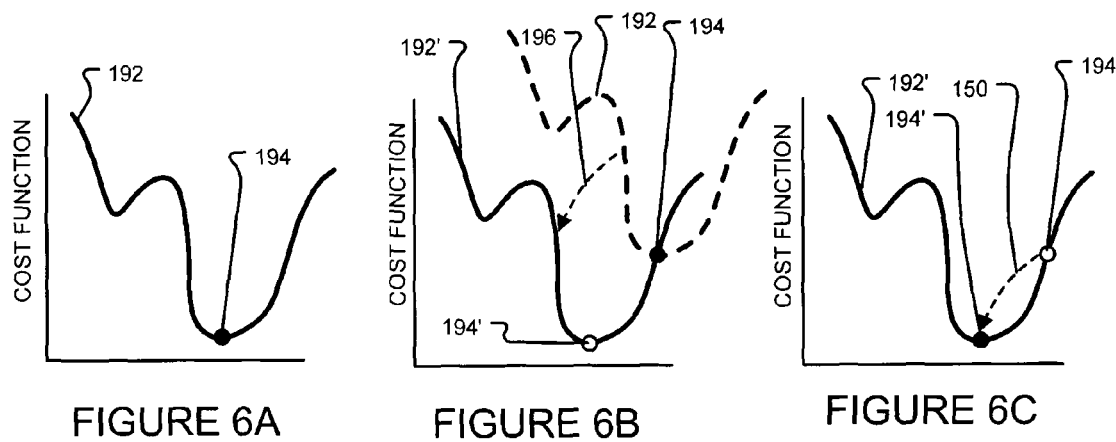
FIGS. 6A, 6B and 6C (collectively, FIG. 6) schematically depict the assumptions which may used to implement relatively rapid fractional optimization in comparison to the initial optimization of the FIG. 2 method.

FIG. 6A schematically depicts a cost function 192 as a function of the radiation delivery variables. The set of radiation delivery variables 194 represents a particular set of radiation delivery variables for which cost function 192 is minimized. The set of radiation delivery variables 194 may represent the initial conditions for the block 150 fractional optimization. As discussed above, initial radiation delivery variables 194 for the block 150 fractional optimization may include those of the radiation treatment plan determined in plan initialization process 102 (i.e. block 130) or those of the previous iteration of block 150. In any event, initial radiation delivery variables 194 shown in FIG. 6A are based on old image data—i.e. the block 110 image data in the case of initial radiation delivery variables 194 determined in block 130 or a previous iteration of block 140 image data in the case of initial radiation delivery variables determined in a previous iteration of block 150.

The acquisition of new image data in block 140 of the current iteration of fractional process 104 causes a shift in the cost function from 192 to 192' as shown by arrow 196 in FIG. 6B. The shift in cost function from 192 to 192' is associated with changes (e.g. movement, deformation or the like) of the target volume and/or non-target tissue which may have occurred between acquisition of the previous image data (on which initial radiation delivery variables are based) and acquisition of the current image data in block 140 of the current iteration of fraction process 104. The block 150 fractional optimization involves finding a new set of radiation delivery variables 194' which correspond to a minimum of shifted cost function 192'. The block 150 fractional optimization is schematically depicted as arrow 150 in FIG. 6C.

The assumptions that the changes in the subject's region of interest between successive imaging procedures are relatively minor and that the block 150 fractional optimization should obtain a further optimized set of radiation delivery variables 194' that is relatively close to its initial set of radiation delivery variables 194 may correspond to the mathematical situation that shifted cost function 192' exhibits no local minima between the initial set of radiation delivery variables 194 and the new set of radiation delivery variables 194'. The assumption that there are no local minima between the initial set of radiation delivery variables 194 and the new set of radiation delivery variables 194' permit the use of several time-saving procedures for the block 150 fractional optimization which would not be suitable or possible for use with the block 130 initial optimization.

In one embodiment, the block 150 fractional optimization makes use of a different mathematical optimization technique than the optimization technique used in the block 130 optimization. Some optimization techniques, such as the gradient method and Newton's method for example, represent relatively "rapid" optimization techniques (e.g. rapid in terms of number of iterations and/or some other measure of computational resources), but are relatively susceptible to the presence of local minima between the initial conditions and the desired solution. Such optimization techniques would typically be unsuitable for use in the block 130 optimization because the block 130 optimization is preferably able to overcome local minima. However, such optimization techniques could be suitable for the block 150 fractional optimization. Accordingly, the block 150 fractional optimization may involve the use of mathematical optimization techniques that are relatively rapid compared to the optimization technique employed in the block 130 initial optimization. Similarly, the block 130 initial optimization may involve the use of mathematical optimization techniques that are relatively more capable of overcoming local minima than the optimization technique employed in the block 150 fractional optimization.

Other embodiments involve reducing the size of the search space in the block 150 fractional optimization relative to the size of the search space in the block 130 initial optimization in order to make the block 150 fractional optimization rapid in relation to the block 130 initial optimization.

In one particular embodiment, reducing the search space of the block 150 fractional optimization involves the use of constraints for the maximum changes of one or more radiation delivery variables between successive iterations of the optimization process. The block 150 fractional optimization may involve using more stringent constraints for the maximum changes of one or more radiation delivery variables between successive iterations of the optimization process when compared to the block 130 initial optimization. For example, where the radiation delivery variables include the MLC leaf positions for each beam, the block 150 fractional optimization may assign maxima (or more stringent maxima) to the changes in the MLC leaf positions between successive iterations of the optimization process.

In one particular embodiment, the block 130 optimization may involve constraints for the maximum changes of one or more radiation delivery variables between successive iterations wherein the inter-iteration constraints on the change(s) to the radiation delivery variable(s) start at an initial maximum and then decrease according to a particular schedule function as the optimization proceeds. In this embodiment, the block 150 inter-iteration constraints on the change(s) to the radiation delivery variable(s) may start at an initial maximum that is less than the initial maximum of the block 130 optimization and may then decrease according to a similar schedule function or according to a different schedule function as the optimization proceeds.

In another embodiment, reducing the search space of the block 150 fractional optimization involves the use of constraints on the maximum aggregate change(s) in one or more of the radiation delivery variables during the block 150 optimization process. The block 150 fractional optimization may involve using more stringent constraints on the maximum aggregate change(s) in one or more of the radiation delivery variables compared to the block 130 initial optimization process. For example, where the radiation delivery variables include the MLC leaf positions for each beam, the block 150 fractional optimization process may assign maxima (or more stringent maxima) to the change of the MLC leaf positions between their initial values and their final (optimized) values.

In one particular embodiment, the block 130 optimization involves the use of constraints on radiation delivery variables that reflect physical limitations. For example, it may not be possible to open a MLC leaf beyond a certain position and it may not be possible to provide negative beam weights. Accordingly, such limitations may impose constraints. In addition, some values of the radiation delivery variables are clearly undesirable (e.g. allowing the MLC leaves to open beyond the projection of the beam' eye view of the target volume) and are imposed as constraints in the block 130 process. In such embodiments, the block 150 fractional optimization may comprise adding new constraints to those used in the block 130 initial optimization. Such new constraints may relate to the radiation delivery variables between their initial values and their final (optimized) values.

In still another embodiment, reducing the search space of the block 150 fractional optimization involves reducing (relative to the block 130 optimization) the randomness of selecting radiation delivery variable(s) for variation in each iteration of the optimization process and/or reducing the randomness of the amount/direction by which the selected radiation delivery variable is varied in each iteration of the optimization process. For example, in some embodiments, each iteration of the block 130 initial optimization involves randomly selecting one or more of: the particular beam in which to vary a radiation delivery variable; the particular radiation delivery variable (e.g. the particular MLC leaf or beam weight) to vary; the direction in which to vary the particular radiation delivery variable to vary; and the amount (amplitude) of variation to apply to the particular radiation variable to vary. In such embodiments, the block 150 fractional optimization may determine the particular beam in which to vary a particular radiation delivery variable for a particular iteration of the optimization process by cycling through each beam in order. The block 150 fractional optimization may also determine, for each beam, the particular radiation delivery variable to vary in a particular iteration of the optimization process by cycling through the MLC leaf positions for the beam and the beam weight in a particular order.

Once the particular radiation delivery variable to vary is decided, then (instead of applying a random change) to the variable, the direction of the change and/or the amount (amplitude) of the change in a particular iteration may be based on the success of one or more previous iteration(s). For example, if it was determined in a previous iteration that moving a particular MLC leaf inwardly cause a corresponding decrease in the cost function, then an adjacent MLC leaf varied in the current iteration may also be moved inwardly. As another example, if it was determined over a number of previous iterations that the rate of decrease of the cost function for a given movement of a particular MLC leaf was decreasing, then an amount of the current movement of that MLC leaf and/or an adjacent MLC leaf could be reduced according to some function.

In still another embodiment, reducing the search space of the block 150 fractional optimization involves changing the criteria (relative to the block 130 criteria) for whether or not a variation of a radiation delivery variable in a particular iteration of the optimization is accepted. In the block 130 initial optimization it is typically desirable to permit some variations of radiation delivery variables in particular iterations of the optimization which actually cause the cost function to increase. This allows the block 130 optimization to escape from local minima in the cost function. For example, in some embodiments, variations of radiation delivery variables which increase the cost function may be permitted with a probability given by the Metropolis condition. In contrast with this aspect of the block 130 initial optimization, in particular embodiments of the block 150 fractional optimization, the variation(s) of radiation delivery variable(s) in a particular iteration may be accepted only when they correspond to decreases in the cost function.

Figure 7:
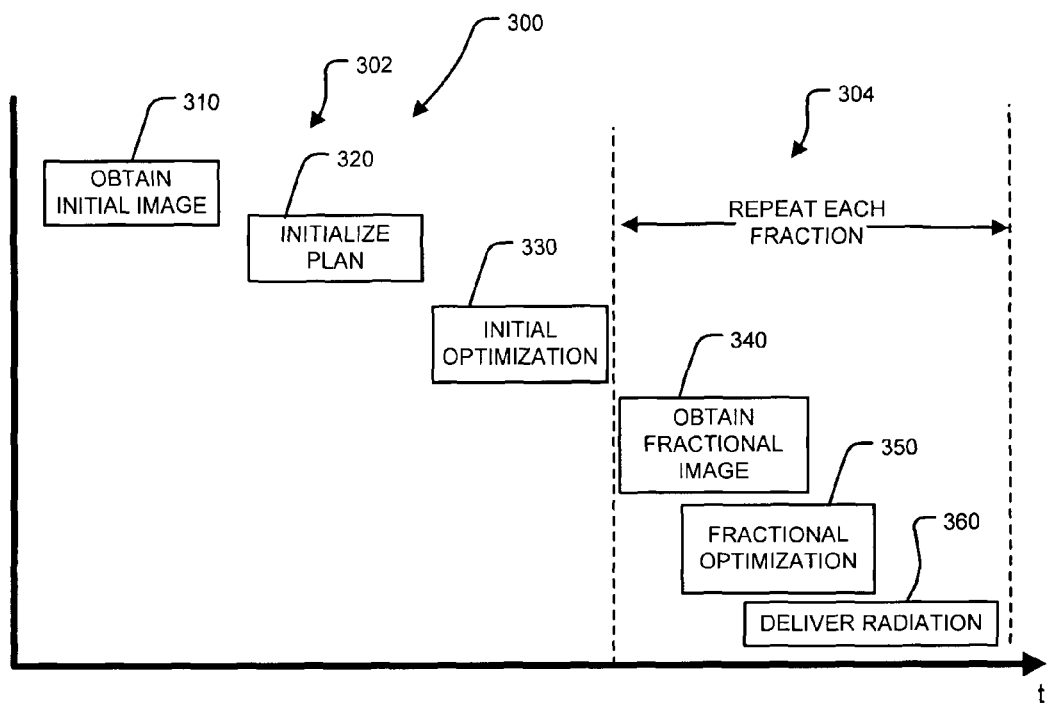
FIG. 7 is a Gantt-type temporal plot showing the timing of the procedures involved in a method for radiation treatment according to another embodiment of the invention.

FIG. 7 is a Gantt-type temporal plot showing the timing of the procedures involved in a method 300 for radiation treatment according to another embodiment of the invention.

Method 300 is similar in many respects to method 100 (FIG. 2) and the reference numbers used to describe the features of method 300 are similar to those used to describe method 100, except that the reference numbers corresponding to the features of method 300 have a leading numeral "3" whereas the reference numbers corresponding to features of method 100 have a leading numeral "1". Method 300 comprises a plan initialization process 302 that is performed once for each subject and a fractional process 304 that is performed once for each fraction of method 300. Plan initialization process 302 may be substantially similar to plan initialization process 102 described herein.

Fractional process 304 of method 300 differs from fractional process 104 of method 100. More particularly, as shown in FIG. 7, portions of the block 340 fractional imaging process 340, the block 350 fractional optimization process and the block 360 fractional radiation delivery process occur simultaneously (i.e. overlap temporally). The temporally overlapping fractional optimization (block 350) and fractional radiation delivery (block 360) may be similar to the temporally overlapping fractional optimization and radiation delivery of blocks 150, 160 described above. However, in method 300, the block 350 fractional optimization commences prior to the completion of the block 340 fractional imaging process.

In one particular embodiment, the block 340 fractional imaging process comprises a tomosynthesis process which may be implemented, for example, by a cone-beam CT imaging apparatus similar to that of imaging system 200 (FIG. 4) described above. In such embodiments, the 360° rotation of the imaging system (e.g. X-ray source 244 and detector unit 238) about the subject may be divided into a plurality of angular portions $P_1, P_2 \ldots P_m$. While the angular portions $P_1, P_2 \ldots P_m$ may be equal to one another, this is not necessary.

In one particular embodiment, each of the angular portions $P_1, P_2 \ldots P_m$ of the block 340 fractional imaging process corresponds to the various beam orientations of the DAO treatment plan beam arrangement. For example, if the beam arrangement of the DAO treatment plan involves delivering one or more beams every 40°, then each portion $P_1, P_2 \ldots P_m$ of the block 340 fractional imaging process may also be 40°. In other embodiments, the first angular portion $P_1$ is relatively large in comparison to the other angular portions $P_2, \ldots P_m$. In one embodiment, the angular portions decrease in size after the first angular portion $P_1$. During each portion $P_1, P_2 \ldots P_m$ of the block 340 fractional imaging process, the imaging system may obtain a plurality of two-dimensional image projections (e.g. X-ray image projections). By way of non-limiting example, the imaging system may obtain a two-dimensional image projection approximately every 1°.

After two dimensional image projections are obtained over the first portion $P_1$, tomosynthesis techniques may be used to reconstruct a three-dimensional image of the region of interest from these image projections. While this three-dimensional reconstructed image may not be of maximum quality at this stage (because of the missing projections from portions $P_2, \ldots P_m$) there may still be enough information to permit the block 350 fractional optimization to commence using the three-dimensional reconstructed image. The block 360 fractional radiation delivery may be permitted to commence after partially completing the block 350 fractional optimization as discussed herein for blocks 150, 160.

In some embodiments, the block 340 fractional image data obtained in portion $P_1$ (or any of the other portions $P_2, \ldots P_m$) may be combined with the block 310 initial image data to provide a higher quality image prior image prior to commencing the block 350 fractional optimization. In embodiments where the angular size of imaging portion $P_1$ corresponds to the angular difference between the various beam orientations of the beam arrangement, the block 350 fractional optimization and the block 360 fractional radiation delivery may be performed for all of the beams at a particular beam orientation after completion of the first imaging portion $P_1$ of the block 340 fractional imaging process, although this is not necessary.

After obtaining image data from portion $P_1$ (and possibly commencing the block 350 fractional optimization and the block 360 fractional radiation delivery), image data may be obtained from portion $P_2$. Image data may be obtained from portion $P_2$ in essentially the same method as image data is obtained from portion $P_1$. After obtaining image data in $P_2$, the image data from portions $P_1$ and $P_2$ may be combined using tomosynthesis methods to generate a three-dimensional reconstructed image. Subsequent portions of the block 350 optimization process may be based on the new reconstructed image which combines the image data from portions $P_1$ and $P_2$. The block 360 fractional radiation delivery continues to follow after partially completing the block 350 fractional optimization as discussed herein for blocks 150, 160. In embodiments where the angular size of imaging portion $P_2$ corresponds to the angular difference between the various beam orientations of the beam arrangement, the block 350 fractional optimization and the block 360 fractional radiation delivery may be performed for all of the beams at a particular beam orientation after completion of the second imaging portion $P_2$ of the block 340 fractional imaging process, although this is not necessary.

The process described above for imaging portions $P_1, P_2$ of the block 340 fractional imaging process (together with the relevant portions of the block 350 fractional optimization and the block 360 fractional radiation delivery) may be repeated for the remaining image portions $P_3, \ldots P_m$.

Figure 8:
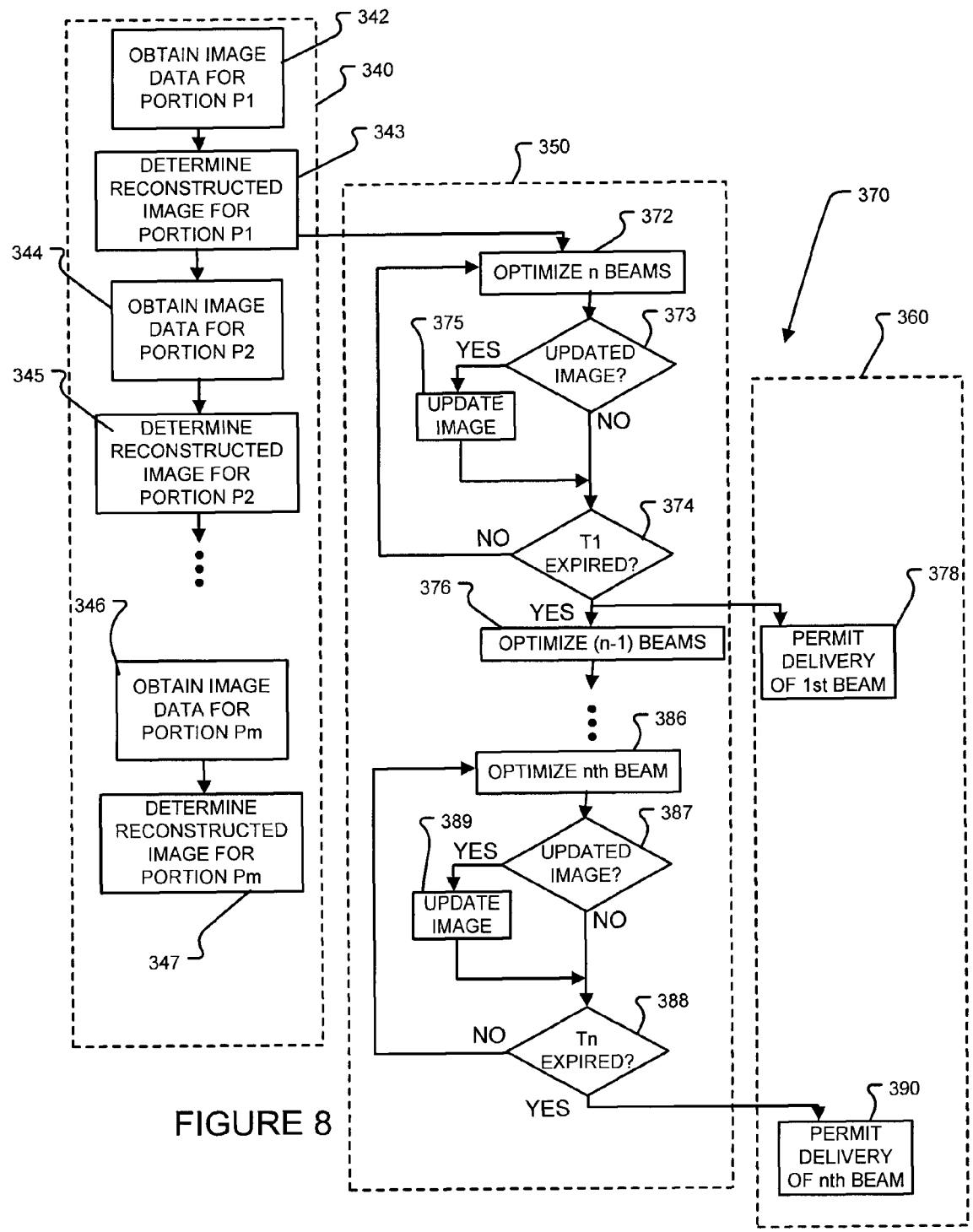
FIG. 8 is a schematic description of the imaging, optimization and radiation delivery procedures of the FIG. 7 method according to a particular embodiment of the invention.

A particular embodiment of the temporally overlapping fractional imaging (block 340), fractional optimization (block 350) and fractional radiation delivery (block 360) is shown schematically as method 370 of FIG. 8. Method 370 commences with the start of the block 340 fractional imaging process. In block 342, image data is obtained for the first portion $P_1$. As discussed above, the block 342 acquisition of image data may comprise acquiring a plurality of two-dimensional projections. Method 370 then proceeds to block 343 which involves determining a reconstructed three-dimensional image using the image data obtained from the portion $P_1$.

Once a reconstructed three-dimensional image is determined in block 343, method 370 may proceed to collect image data from the second portion $P_2$ (block 344), determine a reconstructed three-dimensional image which incorporates the image date acquired in portions $P_1$ and $P_2$ (block 345). Method 370 may continue in this manner to collect image data until portion $P_m$ (block 346). When the three-dimensional image is reconstructed from the image data in portions $P_1, P_2, \ldots P_m$ (block 347), the block 340 fractional image acquisition is complete.

Once the first reconstructed three-dimensional image is determined in block 343, the block 350 optimization can also commence by optimizing the radiation delivery variables for all n beams in block 372. In the illustrated embodiment, the block 350 fractional optimization checks periodically as to whether there is updated three-dimensional image data available (block 373). If there is new three-dimensional image data available (block 373 YES output), then method 370 updates the image data (block 375) and proceeds as discussed herein for method 170. The procedure of checking for updated three-dimensional image data may be performed periodically as beams are removed from the optimization process—see, for example, blocks 387 and 389 of the illustrated embodiment. In other respects, the block 350 optimization and the block 360 radiation delivery of method 370 are similar to the block 150 optimization and the block 160 radiation delivery of method 170.

The particular embodiments described above are applied to DAO radiation treatment and therefore make use of treatment plan parameters and radiation delivery variables that are used in DAO radiation treatment (e.g. the beam arrangement, MLC leaf positions, MLC orientation and beam weight). In general, the invention described herein may be applied to other techniques of radiation treatment which involve different radiation plan parameters and different radiation delivery variables. For example, in some beamlet-based radiation treatment techniques, radiation delivered from each particular beam orientation is broken down into portions (referred to as "beamlets") and the weights of the beamlets are optimized for all the beam orientations in attempt to achieve the objectives of the radiation treatment plan. Thus the beamlet weights may be the radiation delivery variables optimized in the block 110 initial optimization and/or the block 150 fractional optimization.

In such embodiments, once the beamlet weights are optimized for a particular beam orientation, a number of sets of MLC leaf positions and associated beam weights can be derived (on the basis of the optimized beamlet weights) to deliver the optimized beamlets from the particular beam orientation—i.e. the beam orientations represent the control points of beamlet-based radiation treatment. Each set of MLC leaf positions and one associated beam weight correspond to one individual beam from the particular beam orientation. It may be necessary (or desirable) to provide a plurality of individual beams from the particular beam orientation in order to deliver the optimized beamlet weights for that particular beam orientation. The block 150 fractional optimization may involve optimizing the plurality of beamlet weights for a particular beam orientation before deriving the individual beam parameters and permitting the block 160 radiation delivery for that beam orientation (e.g. the periods $T_1$, $T_2, \ldots T_n$ discussed above, could correspond to the period for optimizing the beamlet weights for a particular beam orientation).

It will be appreciated that once the MLC leaf positions and individual beam weights are derived from the optimized beamlets, it may be desirable to use the MLC leaf positions and individual beam weights for future optimizations. In some embodiments, the block 110 initial optimization may comprise optimizing a first set of radiation delivery variables (e.g. beamlet weights) and one or more of the block 150 fractional optimizations may involve optimizing a second set of radiation delivery variables (e.g. MLC leaf positions and individual beam weights), wherein the second set of radiation delivery variables may be determined from the first set of radiation delivery variables.

In other radiation treatment techniques, the beam orientations and/or MLC leaf positions move dynamically while the radiation is being delivered. Non-limiting examples of dynamic delivery techniques include Tomotherapy, Dynamic Conformal Arc Therapy and Intensity Modulated Arc Therapy. In such embodiments, the radiation source is activated while the radiation delivery variables (e.g. MLC positions) are moving in between control points. For such embodiments, when the imaging system is an x-ray imaging system and the x-ray imaging system is integrated with the radiation delivery apparatus the projections $P_1, P_2, \ldots P_n$ may be obtained continuously and simultaneous to the radiation delivery. In this way, new projections can be acquired and used for reconstruction between each control point.

Certain implementations of the invention comprise computer processors which execute software instructions which cause the processors to perform a method of the invention. For example, one or more processors in a dual modulation display system may implement data processing steps in the methods described herein by executing software instructions retrieved from a program memory accessible to the processors. The invention may also be provided in the form of a program product. The program product may comprise any medium which carries a set of computer-readable instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The instructions may be present on the program product in encrypted and/or compressed formats.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

In the literature relating to radiation treatment, the target volume may be referred to as the planning target volume (PTV). The planning target volume is typically larger than the gross target volume (GTV), which represents the exact image volume of the target and the clinical target volume (CTV) which typically includes a volume around the GTV where microscopic amounts of disease may have spread. In this description, the phrase "target volume" should be meant to include the PTV, GTV and/or the CTV as the particular context may warrant.

While radiation treatment system 200 (FIG. 4) represents a particular type of radiation delivery apparatus in conjunction with which the invention may be implemented, it should be understood that the invention may be implemented on different radiation delivery apparatus, the components of which may differ from those of radiation treatment system 200.

As discussed above, MLC 33 (FIG. 4) represents one beam-shaping device which may be incorporated into radiation treatment system 200 and used to implement radiation treatment method 100. It will be appreciated that there are a large number of variations to MLC 33 which may be used in alternative embodiments. MLCs can differ in design details, such as the number of leaves 36, the widths of leaves 36, the shapes of the ends and edges of leaves 36, the range of positions that any leaf 36 can have, constraints on the position of one leaf 36 imposed by the positions of other leaves 36, the mechanical design of the MLC, and the like. The invention described herein should be understood to accommodate any type of configurable beam-shaping apparatus 33 including MLCs having these and other design variations.

In the embodiment described above, the MLC leaf positions and orientations are initialized in block 120 such that the shapes of the resultant beams match a projection of the target volume (e.g. to approximate a beam's eye view outline of the target volume) and the beam weights are initialized in block 120 to have equal values which may be set so that the mean dose in the target volume will equal a prescribed dose objective. In other embodiments, other initialization schemes may be used for the DAO parameters/radiation deliver variables. By way of non-limiting example, the MLC leaf positions may be initialized such that the resultant beams match a boolean projection of the target volume minus the projection(s) of selected healthy tissue/organs.

In the embodiments discussed above, the radiation delivery variables (e.g. the DOA parameters varied during optimization) include the positions of the MLC leaves 36 for each beam and the weight of each beam. As mentioned briefly above, other DAO parameters, such as the orientation of MLC 33 about axis 37 and the characteristics of the beam arrangement (e.g. relative orientations of the radiation source and the subject and the number of beams in each such relative orientation), may be additional or alternative radiation delivery variables. In other radiation treatment techniques, the radiation delivery variables optimized during the block 110 initial optimization and the block 140 fractional optimization may be completely different radiation delivery variables from those described above. Such radiation delivery variables may be particular to the different radiation treatment techniques. In some embodiments, the radiation delivery variables used in the block 110 initial optimization may be different than the radiation delivery variables used in one or more of the block 150 fractional optimizations. In such embodiments, the different radiation delivery variables used in the one or more block 150 fractional optimizations may be derived from the radiation delivery variables used in the block 110 initial optimization.

The description set out above describes optimizing a radiation delivery variables to minimize cost functions. It will be appreciated by those skilled in the art that the optimized set of radiation delivery variables need not strictly coincide with the minimum of the cost function and that the optimized set of radiation variables may comprise a clinically acceptable set of radiation delivery variables which deviate from the absolute minimum of the cost function.

In method 300 of FIG. 7, portions of all three of the block 340 fractional imaging process, the block 350 fractional optimization process and the block 360 fractional radiation delivery process overlap temporally. This is not necessary. In some embodiments, it may be possible for portions of the block 340 fractional imaging process and the block 350 fractional optimization process to overlap temporally, while the block 360 fractional radiation delivery occurs serially after the completion of the block 350 fractional optimization process.

Portions $P_1, P_2 \ldots P_m$ of method 300 described above are described as angular portions. It is not necessary that portions $P_1, P_2 \ldots P_m$ be defined by their angular size. In some embodiments, $P_1, P_2 \ldots P_m$ may be defined temporally, by three-dimensional image reconstruction parameters or otherwise.

In the embodiments described above, three-dimensional images are reconstructed from image data obtained from the most current angular portion and any preceding angular portions. This is not necessary. In some embodiments, only the most recent image data from the most recent angular portion is used to reconstruct the three-dimensional image.

In the embodiments described above, fractional imaging commences at least slightly prior to fractional optimization and fractional optimization commences at least slightly prior to fractional radiation delivery. This is not necessary. In some embodiments, delivery can commence at any time using initial image data and initial optimized radiation delivery variables until such time as new fractional image data and updated fractional radiation delivery variables become available. When fractional image data becomes available, then fractional optimization can commence to obtain fractional updates to the radiation delivery variables. When fractional updates for the radiation delivery variables are available, these fractional updates can be incorporated into the fractional radiation delivery.

What is claimed is:

1. A method for radiation treatment of a subject involving one or more fractional treatments, the method comprising, for at least one fractional treatment:
    obtaining fractional image data pertaining to a region of interest of the subject;
    performing a fractional optimization of a radiation treatment plan to determine optimized values of one or more radiation delivery variables, the fractional optimization based at least in part on the fractional image data; and
    delivering a fraction of the radiation treatment plan to the region of interest using the optimized values of the one or more radiation delivery variables as one or more corresponding parameters of the radiation treatment plan;
    wherein a portion of performing the fractional optimization overlaps temporally with a portion of at least one of: obtaining the fractional image data and delivering the fraction of the radiation treatment plan.

2. A method according to claim 1 wherein performing the fractional optimization comprises varying values of the one or more radiation delivery variables so as to minimize a cost function to at least a clinically acceptable level and wherein the region of interest comprises a target volume and at least some tissue from a region outside of the target volume and wherein the cost function increases when at least one of:
    a radiation dose estimated to be delivered to the target volume is below a minimum target threshold ($D_{min}$) or above a maximum target threshold ($D_{max}$); and
    a radiation dose estimated to be delivered to a region of healthy tissue outside of the target volume is above a maximum non-target threshold ($D_1$).

3. A method according to claim 1 comprising developing an initial radiation treatment plan prior to performing the at least one fractional treatment.

4. A method according to claim 3 wherein developing the initial radiation treatment plan comprises:
    obtaining initial image data pertaining to the region of interest of the subject; and
    performing initial optimization of the initial radiation treatment plan to determine optimized initial values of one or more initial variables, the initial optimization based at least in part on the initial image data.

5. A method according to claim 4 wherein the one or more radiation delivery variables are the same as the one or more initial variables.

6. A method according to claim 5 wherein the at least one fractional treatment comprises a plurality of fractional treatments.

7. A method according to claim 6 wherein performing the fractional optimization in the first of the plurality of fractional treatments comprises using the optimized initial values as fractional initial values of the one or more radiation delivery variables for performing the fractional optimization in the first of the plurality of fractional treatments.

8. A method according to claim 7 wherein performing the fractional optimization in the second and subsequent ones of the plurality of fractional treatments comprises using the optimized initial values as fractional initial values of the one or more radiation delivery variables for performing the fractional optimization in the second and subsequent ones of the plurality of fractional treatments.

9. A method according to claim 7 wherein performing the fractional optimization in the second and subsequent ones of the plurality of fractional treatments involves using the optimized values of the one or more radiation delivery variables from a preceding one of the plurality of fractional treatments as fractional initial values of the one or more radiation delivery variables for performing the fractional optimization in the second and subsequent ones of the plurality of fractional treatments.

10. A method according to claim 6 wherein performing the initial optimization comprises using a first optimization technique and performing the fractional optimization comprises using a second optimization technique and wherein the first and second optimization techniques differ from one another.

11. A method according to claim 10 wherein the first optimization technique is relatively more capable of overcoming local cost function minima than the second optimization technique.

12. A method according to claim 10 wherein the first optimization technique consumes a relatively large amount of computational resources to complete an optimization process when compared to the second optimization technique.

13. A method according to claim 10 wherein the first optimization technique comprises occasionally permitting variations of the values of the one or more radiation delivery variables which result in cost function increases and wherein the second optimization technique comprises rejecting variations of the values of the one or more radiation delivery variables which result in cost function increases.

14. A method according to claim 10 wherein the first optimization technique comprises iteratively varying the values of the one or more radiation delivery variables in a random order and the second optimization technique comprises iteratively varying the values of the one or more radiation delivery variables in a specific order.

15. A method according to claim 10 wherein the second optimization technique comprises a constraint of a maximum inter-iteration variation of the values of the one or more radiation delivery variables between successive iterations.

16. A method according to claim 15 wherein the first optimization technique also comprises a constraint of a maximum inter-iteration variation of the values of the one or more radiation delivery variables between successive iterations and wherein the maximum inter-iteration variation associated with the second optimization technique is less than the maximum inter-iteration variation associated with the first optimization technique.

17. A method according to claim 10 wherein the second optimization technique comprises one or more constraints which comprise maximum aggregate changes for the values of the one or more radiation delivery variables between their initial values and their optimized values.

18. A method according to claim 10 wherein the second optimization technique comprises, after selecting a radiation delivery variable to vary for a particular iteration, varying the selected radiation delivery variable in a direction according to: if a direction of the variation of a previously varied radiation delivery variable resulted in a decrease in the cost function, then varying the selected radiation delivery variable in the same direction as the variation of the previously varied radiation delivery variable; and if the direction of the variation of the previously varied radiation delivery variable resulted in an increase in the cost function, the varying the selected radiation delivery variable in an opposite direction to the variation of the previously varied radiation delivery variable.

19. A method according to claim 1 wherein portions of performing the fractional optimization and delivering the fraction of the radiation treatment plan overlap temporally.

20. A method according to claim 1 wherein portions of obtaining fractional image data and performing the fractional optimization overlap temporally.

21. A method for radiation treatment of a subject involving one or more fractional treatments, the method comprising, for at least one fractional treatment:
  obtaining fractional image data pertaining to a region of interest of the subject;
  performing a fractional optimization of a radiation treatment plan to determine optimized values of one or more radiation delivery variables, the fractional optimization based at least in part on the fractional image data; and
  delivering a fraction of the radiation treatment plan to the region of interest using the optimized values of the one or more radiation delivery variables as one or more corresponding parameters of the radiation treatment plan;
  wherein portions of performing the fractional optimization and delivering the fraction of the radiation treatment plan overlap temporally; and
  wherein performing the fractional optimization and delivering the fraction of the radiation treatment plan comprise:
  (a) optimizing values of the one or more radiation delivery variables corresponding to each of a group of control points for an optimization period;
  (b) after the optimization period:
    (i) fixing the values of the one or more radiation delivery variables corresponding to one of the control points to be the optimized values of the one or more radiation delivery variables corresponding to the one of the control points;
    (ii) permitting delivery of radiation corresponding to the one of the control points using the optimized values of the one or more radiation delivery variables corresponding to the one of the control points; and
    (iii) removing the one of the control points from the group of control points.

22. A method according to claim 21 comprising iteratively repeating steps (a), (b)(i), b(ii) and (b)(iii) of claim 21.

23. A method according to claim 22 wherein each control point in the group of control points corresponds to an individual radiation beam in a direct aperture optimization (DAO) radiation treatment process.

24. A method according to claim 22 wherein the one or more radiation delivery variables corresponding to each control point comprise one or more of: a weight of a beam in a direct aperture optimization (DAO) radiation treatment process; positions of multi-leaf collimator (MLC) leaves for a beam in a DAO radiation treatment process; and a pivotal orientation of a MLC for a beam in a DAO radiation treatment process.

25. A method according to claim 22 wherein each control point in the group of control points corresponds to a beam orientation in a beamlet-based radiation treatment process.

26. A method according to claim 25 wherein the one or more radiation delivery variables corresponding to each control point comprise weights of beamlets for the beam orientation corresponding to the control point.

27. A method according to claim 26 wherein the one or more radiation delivery variables corresponding to each control point comprise: a weight of a particular beam; positions of multi-leaf collimator (MLC) leaves for a particular beam; and a pivotal orientation of a MLC for a particular beam.

28. A method according to claim 22 wherein the optimization period comprises, for each repetition of steps (a), (b)(i), b(ii) and (b)(iii), at least one of: a threshold number of iterations of the step (a) optimization; a threshold time; achievement of a threshold level of optimization as determined by evaluation of a cost function; and achievement of a threshold rate of change of optimization as determined by evaluation of a rate of change of a cost function.

29. A method according to claim 28 wherein the optimization period is the same for each repetition of steps (a), (b)(i), b(ii) and (b)(iii).

30. A method according to claim 28 wherein the optimization period is different for at least two repetitions of steps (a), (b)(i), b(ii) and (b)(iii).

31. A method according to claim 22 comprising, after each iteration of step (b)(ii), delivering radiation corresponding to the one of the control points using the optimized values of the one or more radiation delivery variables corresponding to the one of the control points.

32. A method according to claim 31 wherein the optimization period for each of the second and subsequent repetitions of steps (a), (b)(i), (b)(ii), (b)(iii) is less than or equal to the time for delivering radiation corresponding to the control point removed from the group of control points in the previous iteration.

33. A method according to claim 31 wherein the optimization period for each of the second and subsequent repetitions of steps (a), (b)(i), (b)(ii), (b)(iii) is set at the time required for delivering radiation corresponding to the control point removed from the group of control points in the previous iteration.

34. A method according to claim 21 comprising iteratively repeating steps (a), (b)(i), (b)(ii) and (b)(iii) of claim 21 until all of the control points have been removed from the group of control points.

35. A method for radiation treatment of a subject involving one or more fractional treatments, the method comprising, for at least one fractional treatment:
  obtaining fractional image data pertaining to a region of interest of the subject;
  performing a fractional optimization of a radiation treatment plan to determine optimized values of one or more radiation delivery variables, the fractional optimization based at least in part on the fractional image data; and
  delivering a fraction of the radiation treatment plan to the region of interest using the optimized values of the one or more radiation delivery variables as one or more corresponding parameters of the radiation treatment plan;
  wherein portions of obtaining fractional image data and performing the fractional optimization overlap temporally; and
  wherein obtaining fractional image data comprises successively obtaining a plurality of image data portions and, after obtaining each image data portion, reconstructing a corresponding three-dimensional representation of the region of interest based, at least in part, on the image data portion.

36. A method according to claim 35 wherein reconstructing the corresponding three-dimensional representation of the region of interest is based, at least in part, on a combination of the image data portion and any preceding image data portions.

37. A method according to claim 35 wherein successively obtaining a plurality of image data portions comprises, for each image data portion, obtaining one or more corresponding two-dimensional projections from a corresponding angular region around the subject.

38. A method according to claim 37 wherein each corresponding angular region is of substantially the same size.

39. A method according to claim 37 wherein a first corresponding angular region is larger than successive angular regions.

40. A method according to claim 37 wherein delivering the fraction of the radiation treatment plan to the region of interest comprises delivering radiation from a plurality of beam orientations and wherein the corresponding angular regions correspond to a spacing between the beam orientations.

41. A method according to claim 35 comprising, after obtaining a first image data portion and reconstructing a first three-dimensional representation of the region of interest, commencing the fractional optimization using the first three-dimensional representation of the region of interest prior to completing obtaining a second image data portion.

42. A method according to claim 41 wherein reconstructing the first three-dimensional representation of the region of interest is based at least in part on initial image data obtained prior to obtaining the first image data portion.

43. A method according to claim 42 comprising, after obtaining the second image data portion and reconstructing a second three-dimensional representation of the region of interest, continuing the fractional optimization using the second three-dimensional representation of the region of interest prior to completing obtaining a third image data portion.

44. A method according to claim 35 wherein each of the image data portions are of substantially the same size.

45. A method according to claim 35 wherein a first image data portion is larger than successive image data portions.

46. A method according to claim 35 wherein portions of performing the fractional optimization and delivering the fraction of the radiation treatment plan overlap temporally.

47. A method according to claim 46 wherein performing the fractional optimization and delivering the fraction of the radiation treatment plan comprise:
  (a) optimizing values of the one or more radiation delivery variables corresponding to each of a group of control points for an optimization period;
  (b) after the optimization period:
    (i) fixing the values of the one or more radiation delivery variables corresponding to one of the control points to be the optimized values of the one or more radiation delivery variables corresponding to the one of the control points;

(ii) permitting delivery of radiation corresponding to the one of the control points using the optimized values of the one or more radiation delivery variables corresponding to the one of the control points; and (iii) removing the one of the control points from the group of control points.

48. A method according to claim 47 comprising iteratively repeating steps (a), (b)(i), b(ii) and (b)(iii) of claim 48.

49. A method for radiation treatment of a subject involving one or more fractional treatments, the method comprising:
    obtaining initial image data pertaining to a region of interest of the subject;
    performing initial optimization of an initial radiation treatment plan to determine optimized initial values of one or more initial variables, the initial optimization based at least in part on the initial image data; and
    for at least one fractional treatment:
        obtaining fractional image data pertaining to the region of interest of the subject;
        performing a fractional optimization of a radiation treatment plan to determine optimized values of one or more radiation delivery variables, the fractional optimization based at least in part on the fractional image data; and
        delivering a fraction of the radiation treatment plan to the region of interest using the optimized values of the one or more radiation delivery variables as one or more corresponding parameters of the radiation treatment plan;
    wherein performing the initial optimization comprises using a first optimization technique and performing the fractional optimization comprises using a second optimization technique and wherein the first and second optimization techniques differ from one another.

50. A method according to claim 49 wherein the first optimization technique is relatively more capable of overcoming local cost function minima than the second optimization technique.

51. A method according to claim 49 wherein the first optimization technique consumes a relatively large amount of computational resources to complete an optimization process when compared to the second optimization technique.

52. A method according to claim 49 wherein the first optimization technique comprises occasionally permitting variations of the values of the one or more radiation delivery variables which result in cost function increases and wherein the second optimization technique comprises rejecting variations of the values of the one or more radiation delivery variables which result in cost function increases.

53. A method according to claim 49 wherein the first optimization technique comprises iteratively varying the values of the one or more radiation delivery variables in a random order and the second optimization technique comprises iteratively varying the values of the one or more radiation delivery variables in a specific order.

54. A method according to claim 49 wherein the second optimization technique comprises a constraint of a maximum inter-iteration variation of the values of the one or more radiation delivery variables between successive iterations.

55. A method according to claim 54 wherein the first optimization technique also comprises a constraint of a maximum inter-iteration variation of the values of the one or more radiation delivery variables between successive iterations and wherein the maximum inter-iteration variation associated with the second optimization technique is less than the maximum inter-iteration variation associated with the first optimization technique.

56. A method according to claim 49 wherein the second optimization technique comprises one or more constraints which comprise maximum aggregate changes for the values of the one or more radiation delivery variables between their initial values and their optimized values.

57. A method according to claim 49 wherein the second optimization technique comprises, after selecting a radiation delivery variable to vary for a particular iteration, varying the selected radiation delivery variable in a direction according to: if a direction of the variation of a previously varied radiation delivery variable resulted in a decrease in the cost function, then varying the selected radiation delivery variable in the same direction as the variation of the previously varied radiation delivery variable; and if the direction of the variation of the previously varied radiation delivery variable resulted in an increase in the cost function, the varying the selected radiation delivery variable in an opposite direction to the variation of the previously varied radiation delivery variable.

58. A computer program product comprising a non-transitory computer readable medium encoded with code segments for controlling a radiation treatment system to provide one or more fractional radiation treatments to a subject, the radiation treatment system comprising an imaging system and a radiation delivery system, the code segments configured to direct one or more processors, for at least one fraction, to:
    cause the imaging system to obtain fractional image data pertaining to a region of interest of the subject;
    perform a fractional optimization of a radiation treatment plan to determine optimized values of one or more radiation delivery variables, the fractional optimization based at least in part on the fractional image data; and
    cause the radiation delivery system to deliver a fraction of the radiation treatment plan to the region of interest using the optimized values of the one or more radiation delivery variables as one or more corresponding parameters of the radiation treatment plan;
    wherein a portion of performing the fractional optimization overlaps temporally with a portion of at least one of: obtaining the fractional image data and delivering the fraction of the radiation treatment plan.

59. A computer program product comprising a non-transitory computer readable medium encoded with code segments for controlling a radiation treatment system to provide one or more fractional radiation treatments to a subject, the one or more fractional radiation treatments occurring after obtaining initial image data pertaining to a region of interest of the subject and performing initial optimization of an initial radiation treatment plan to determine optimized initial values of one or more initial variables based at least in part on the initial image data, the radiation treatment system comprising an imaging system and a radiation delivery system, the code segments configured to direct one or more processors, for at least one fraction, to:
    cause the imaging system to obtain fractional image data pertaining to the region of interest of the subject;
    perform a fractional optimization of a radiation treatment plan to determine optimized values of one or more radiation delivery variables, the fractional optimization based at least in part on the fractional image data; and
    cause the radiation delivery system to deliver a fraction of the radiation treatment plan to the region of interest using the optimized values of the one or more radiation delivery variables as one or more corresponding parameters of the radiation treatment plan;
    wherein performing the initial optimization comprises using a first optimization technique and performing the fractional optimization comprises using a second optimization technique and wherein the first and second optimization techniques differ from one another.

60. A radiation treatment system for providing one or more fractional radiation treatments to a subject, the radiation treatment system comprising:
- an imaging system for obtaining images of a region of interest of the subject;
- a radiation delivery system for delivering radiation to the region of interest of the subject;
- a controller connected to the imaging system and to the radiation delivery system and configured, for at least one fraction, to:
- cause the imaging system to obtain fractional image data pertaining to the region of interest of the subject;
- perform a fractional optimization of a radiation treatment plan to determine optimized values of one or more radiation delivery variables, the fractional optimization based at least in part on the fractional image data; and
- cause the radiation delivery system to deliver a fraction of the radiation treatment plan to the region of interest using the optimized values of the one or more radiation delivery variables as one or more corresponding parameters of the radiation treatment plan;
- wherein a portion of performing the fractional optimization overlaps temporally with a portion of at least one of: obtaining the fractional image data and delivering the fraction of the radiation treatment plan.

61. A radiation treatment system for providing one or more fractional radiation treatments to a subject, the one or more fractional radiation treatments occurring after obtaining initial image data pertaining to a region of interest of the subject and performing initial optimization of an initial radiation treatment plan to determine optimized initial values of one or more initial variables based at least in part on the initial image data, the radiation treatment system comprising:
- an imaging system for obtaining images of a region of interest of the subject;
- a radiation delivery system for delivering radiation to the region of interest of the subject;
- a controller connected to the imaging system and to the radiation delivery system and configured, for at least one fraction, to:
- cause the imaging system to obtain fractional image data pertaining to the region of interest of the subject;
- perform a fractional optimization of a radiation treatment plan to determine optimized values of one or more radiation delivery variables, the fractional optimization based at least in part on the fractional image data; and
- cause the radiation delivery system to deliver a fraction of the radiation treatment plan to the region of interest using the optimized values of the one or more radiation delivery variables as one or more corresponding parameters of the radiation treatment plan;
- wherein performing the initial optimization comprises using a first optimization technique and performing the fractional optimization comprises using a second optimization technique and wherein the first and second optimization techniques differ from one another.

* * * * *